United States Patent
Inada

(12) United States Patent (10) Patent No.: US 7,126,120 B2
(45) Date of Patent: Oct. 24, 2006

(54) ELECTRON MICROSCOPE

(75) Inventor: Hiromi Inada, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 10/951,892

(22) Filed: Sep. 29, 2004

(65) Prior Publication Data

US 2005/0072920 A1 Apr. 7, 2005

(30) Foreign Application Priority Data

Sep. 29, 2003 (JP) .................................. 2003-338687

(51) Int. Cl.
*G01N 23/00* (2006.01)
*G21K 7/00* (2006.01)

(52) U.S. Cl. .................. 250/307; 250/311; 356/401; 356/372

(58) Field of Classification Search ........... 250/311, 250/307, 310; 356/401, 372
See application file for complete search history.

(56) References Cited

U.S. PATENT DOCUMENTS

| | | | |
|---|---|---|---|
| 5,313,062 A | 5/1994 | Yamada | |
| 6,067,164 A | 5/2000 | Onoguchi et al. | |
| 2005/0035290 A1 * | 2/2005 | Saitoh | ........................ 250/307 |

FOREIGN PATENT DOCUMENTS

| | | |
|---|---|---|
| JP | 61-281446 | 12/1988 |
| JP | 5-234555 | 9/1993 |
| JP | 3021917 | 1/2000 |
| JP | 2001-68048 | 3/2001 |

OTHER PUBLICATIONS

Krivanek, O.L., et al., "Applications of slow–scan CCD cameras in transmission electron microscopy" Ultramicroscopy, 49 (1993), pp. 95–108.

* cited by examiner

*Primary Examiner*—Jack Berman
*Assistant Examiner*—Zia R. Hashmi
(74) *Attorney, Agent, or Firm*—McDermott Will & Emery LLP

(57) ABSTRACT

In an electron microscope, focus correction is carried out automatically, an astigmatic difference amount is displayed and astigmatism correction is executed quantitatively. Enlarged specimen images obtained by irradiating an electron beam on a specimen while changing excitation currents of an objective lens and of a stigmator coil are picked up by a capturing unit comprised of an optical lens and a capturing device and image sharpness coefficients are calculated by means of an arithmetic logic unit. A suitable astigmatism correction direction is chosen on the basis of an angular component value of the obtained image sharpness coefficients and then, a correction excitation current is supplied to a stigmator coil to correct astigmatism and a correction excitation current is supplied to an objective lens coil to perform focus correction.

16 Claims, 23 Drawing Sheets

ORIGINAL IMAGE

CONTRAST

COORDINATES X

ORIGINAL IMAGE LINE PROFILE

D(CONTRAST)/DX

COORDINATES X

FIRST ORDER DIFFERENTIAL
IMAGE LINE PROFILE

EDGE ENHANCED IMAGE

D2(CONTRAST)/DX2

COORDINATES X

SECOND ORDER DIFFERENTIAL
IMAGE LINE PROFILE

FIG.9A

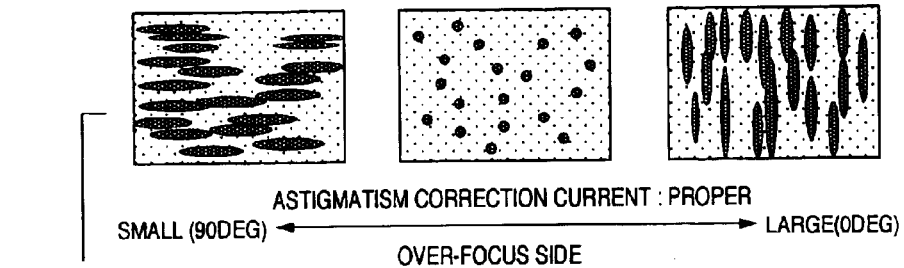

ASTIGMATISM CORRECTION CURRENT : PROPER
SMALL (90DEG) ◄——————— OVER-FOCUS SIDE ———————► LARGE(0DEG)

X ASTIGMATISM SIDE

FIG.9B

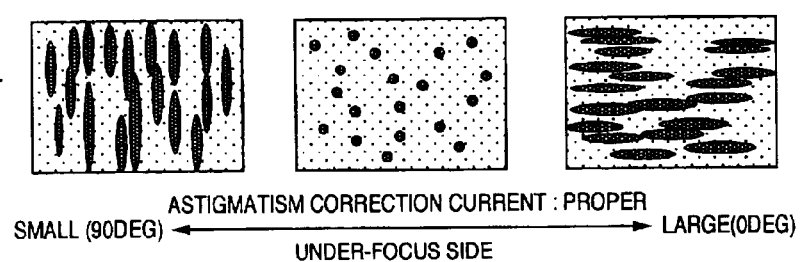

ASTIGMATISM CORRECTION CURRENT : PROPER
SMALL (90DEG) ◄——————— UNDER-FOCUS SIDE ———————► LARGE(0DEG)

FIG.9C

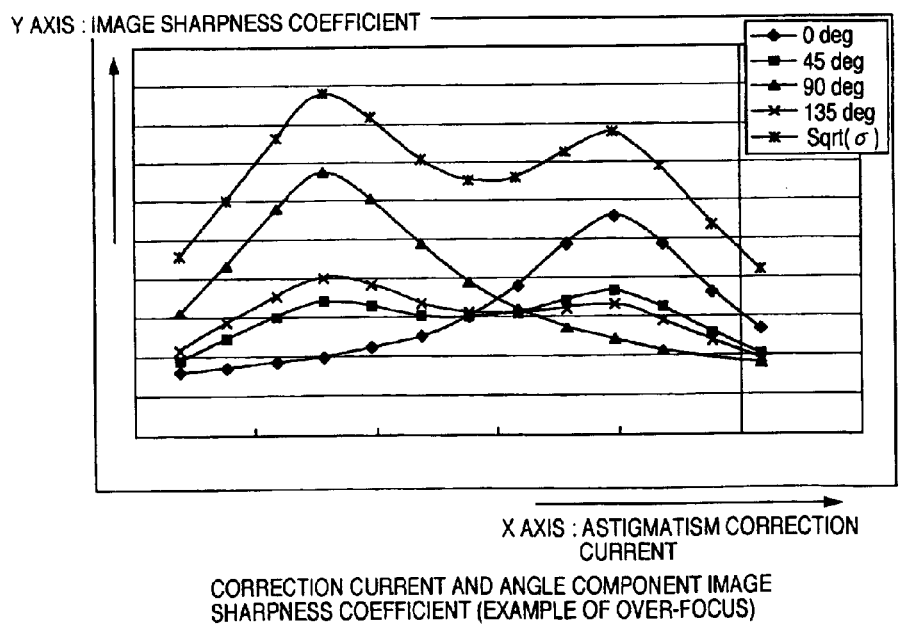

Y AXIS : IMAGE SHARPNESS COEFFICIENT

- 0 deg
- 45 deg
- 90 deg
- 135 deg
- Sqrt($\sigma$)

X AXIS : ASTIGMATISM CORRECTION CURRENT

CORRECTION CURRENT AND ANGLE COMPONENT IMAGE
SHARPNESS COEFFICIENT (EXAMPLE OF OVER-FOCUS)

ASTIGMATISM CORRECTION CURRENT : PROPER

SMALL (90DEG) ←———————————→ LARGE(0DEG)
OVER-FOCUS SIDE

Y ASTIGMATISM SIDE

ASTIGMATISM CORRECTION CURRENT : PROPER

SMALL (90DEG) ←———————————→ LARGE(0DEG)
UNDER-FOCUS SIDE

CORRECTION CURRENT AND ANGLE COMPONENT IMAGE SHARPNESS
COEFFICIENT ON Y ASTIGMATISM SIDE (EXAMPLE OF OVER-FOCUS)

UNPROCESSED MEASUREMENT RESULT
IMAGE SHARPNESS COEFFICIENT V

PERR POINT

PTRUE POINT

LENS CURRENT VALUE

PIXEL MEAN VALUE SUM
PIXEL MEAN VALUE AV

LENS CURRENT VALUE

DIVISION BY PIXEL MEAN VALUE
SHARPNESS COEFFICIENT V/MEAN VALUE AV

LENS CURRENT VALUE

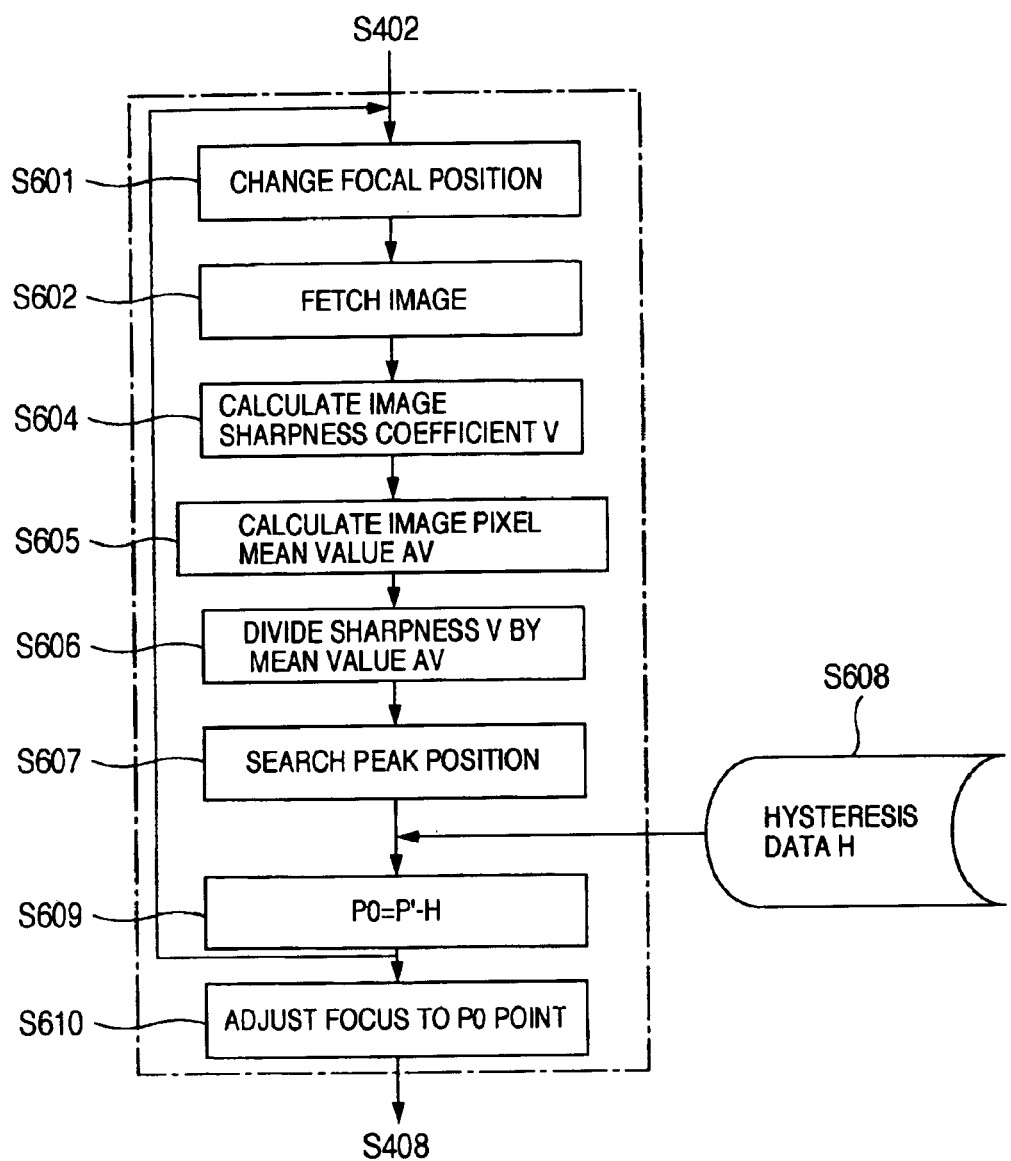

$\mu 1$
$I = I_1$

IMAGE EXAMPLE IN THE
PRESENCE OF ASTIGMATISM $\mu\,opt$
$I = I\,opt$

IMAGE EXAMPLE IN THE
ABSENCE OF ASTIGMATISM

PRESENCE OR ABSENCE OF ASTIGMATISM AND HYSTOGRAM

ELECTRON MICROSCOPE

BACKGROUND OF THE INVENTION

The present invention relates to electron microscopes and more particularly, to an electron microscope capable of automatically adjusting the focus of an electron lens and astigmatism of an electron beam.

Conventionally, in observing, measuring, analyzing and searching a field of view of an enlarged specimen image with an electron microscope, an operator participates in performing focusing and astigmatism adjustment while directly watching the enlarged specimen image. In adjusting focus and astigmatism, while the focus correction is carried out in the direction of height of a specimen (referred to as Z direction), the astigmatism correction is carried out in respect of astigmatic aberrations in 0° and 90° directions (X direction) of the specimen and in respect of astigmatic aberrations in 45° and 135° directions (Y direction) of the specimen and therefore adjustments in three directions in total must be accomplished. Namely, when only the focus correction is completed but any astigmatism remains, the enlarged specimen image becomes blurred, resulting in degradation of image quality and inaccuracy of analytical position. It has been practice that the operator participating in the focus and astigmatism adjustments identifies a focus offset and an astigmatic offset while watching an enlarged specimen image. Generally, for the focus correction, excitation current of an objective lens coil serving as an electron lens is changed and for the astigmatism correction, excitation current is supplied to a stigmator coil.

A method for automatically performing focusing is disclosed in, for example, JP-A-61-281446, according to which the focus correction is carried out by deflecting and tilting an electron beam, failing to perform the astigmatism correction and besides the electron beam is so conditioned as to transmit through the specimen.

A focusing and astigmatism adjustment method using a CCD camera is discussed in Ultramicroscopy 49 (1993), pp95–108 but in the method, the specimen is limited to amorphous thin films and besides, operational magnification is limited to high magnification at which the amorphous structure explicitly exhibits itself.

Also, in JP-A-2001-68048 and Japanese Patent No. 3021917, a method for automatic focusing and astigmatism correction is disclosed, which gives a description of astigmatism correction operation but fails to quantitatively determine an astigmatic difference amount and quantitatively decide steady completion of astigmatism correction, thus relying on the level of operational skillfulness of operator.

SUMMARY OF THE INVENTION

A first problem to be solved by this invention is to automate focusing and astigmatism correction which have hitherto been performed manually by an operator. The principle of astigmatism will be explained by making reference to FIG. 2. When a magnetic field forming an electron lens is not rotationally symmetric, the focal distance of an electron beam differs in X-axis and Y-axis directions as shown in FIG. 2 and astigmatic aberrations take place. Enumerated as causes of generation of the astigmatism are accuracy of mechanical working of the electron lens, charge-up on a specimen or specimen stage or non-uniformity thereof, circle roundness of an aperture bore and charge-up due to contamination on the aperture bore. In the presence of the astigmatism, the electron beam is not round circular but is elliptical in cross section as shown at a1 and a3 in FIG. 2 and an enlarged specimen image is elongated as shown at a1' and a3'. In correction of the astigmatism, an excitation current is supplied to an atigmator coil to correct an elongation of the electron beam cross section, thus shaping the electron beam into a round circular one. But, in case the astigmatism correction is tried under a greatly defocused condition, the enlarged specimen image has a low image contrast and the astigmatism correction direction becomes very difficult to discriminate. On the other hand, when the focus correction is performed under a condition that a large astigmatic aberration exists, the image contrast of an image is lowered similarly and determination of an exact focus position is difficult to achieve. In other words, when only the focus correction is completed and the astigmatism remains, the enlarged specimen image becomes blurred, giving rise to degradation of image quality and inaccuracy of analytical position. In operator-based adjustment, the operator must adjust three of focus, X-direction astigmatism and Y-direction astigmatism at a time while deciding the contrast of image and for an operator having poor experience, the adjustment is complicated and sophisticated and difficult to perform. Accordingly, the present invention has its object to provide an electron microscope capable of making focus correction and astigmatism correction automatically and highly accurately.

A second problem to be solved by this invention is that when the astigmatism is large, the image blur is aggravated and a sufficient image sharpness coefficient cannot be obtained. In case the electron optical condition of electron microscope changes to cause the astigmatism to change to a great extent, the image blur grows extensively and both the astigmatism and focus correction adjustments cannot sometimes follow. Then, another object of this invention is to provide an electron microscope capable of finding a proper astigmatism correction value and automatically performing focus and astigmatism corrections.

A third problem to be solved by this invention is that when objective lens coil current and stigmator coil current are adjusted toward an exact focus position with an electron microscope for performing auto focusing and auto astigmatism correction, focusing to the exact focus position cannot be done properly owing to hysteresis of a ferromagnetic material used for the lens coil. There is also a problem that when an image average integration filter is used in order to speed up the image capture or pickup and improve the S/N ratio, past information is superimposed on an image and as a result, an offset is caused in correction current. Then, another object of this invention is to provide an electron microscope capable of supplying suitable objective lens coil current and stigmator coil current without being affected by the hysteresis.

A fourth problem to be solved by this invention is that in the electron microscope for performing auto focusing and auto astigmatism correction, the presence of defocusing or focus offset and astigmatic aberration degrades or lowers the contrast of an enlarged specimen image, with the result that positional alignment with a correct focus correction position and astigmatism correction position is prevented. Accordingly, a still another object of this invention is to provide an electron microscope capable of supplying suitable objective lens coil current and stigmator coil current even when the contrast of an image is low owing to the focus offset and astigmatic aberration.

A fifth problem to be solved by this invention is that in practicing auto astigmatism correction by using the electron microscope for performing auto astigmatism correction, an amount of astigmatic aberration at present cannot be recognized by an operator and therefore the operator must set and conclude an astigmatism correction search range every correction operation. Accordingly, a still another object of this invention is to provide an electron microscope capable of providing a suitable astigmatism correction search range when performing auto astigmatism correction.

A sixth problem to be solved by this invention is that in performing astigmatism correction in the electron microscope, an operator must decide qualitatively and subjectively, from an image captured and observed by the operator, whether the astigmatism correction is completed. Accordingly, still another object of this invention is to provide an electron microscope capable of deciding whether astigmatism correction is completed.

According to the present invention, to solve the first problem, images are recorded by changing focal position and astigmatism correction current and focus correction and astigmatism correction are carried out automatically and highly accurately on the basis of image sharpness coefficients of the images. To solve the second problem, images are recorded by changing focal position and astigmatism correction current, a suitable astigmatism correction value is found from image sharpness coefficients and pixel average values and the focus correction and astigmatism correction are carried out automatically. To solve the third problem, a hysteresis phenomenon is corrected to provide suitable objective lens coil current and stigmator coil current. To solve the fourth problem, suitable objective lens coil current and stigmaror coil current are given through above-mentioned calculation of the image value when an image of low image contrast is handled. To solve the fifth problem, in performing auto astigmatism correction, an astigmatic difference amount is calculated to provide a suitable astigmatism correction search range. To solve the sixth problem, in performing auto astigmatism correction, an astigmatic difference amount is calculated and the astigmatic difference amount is displayed quantitatively and besides compared with a threshold value to decide whether the astigmatism correction is completed.

More particularly, a specimen observing method based on an electron microscope according to this invention comprises a step of picking up enlarged specimen images by changing focal position of an electron beam on the specimen and a step of deciding the number of peaks on a curve indicative of the relation between focal position of the electron beam and image sharpness coefficient and when two peaks are determined in the decision, an astigmatism correction process proceeds, wherein the stigmatism correction process includes a step of picking up enlarged specimen images by changing astigmatism correction current of a stigmaror in X direction, a step of image-calculating image sharpness coefficients of the enlarged specimen images, a step of determining a minimum position sandwiched by two peaks on a curve indicative of the relation between astigmatism correction current of the stigmator in X direction and image sharpness coefficient, a step of setting the astigmatism correction current of the stigmator in X direction to a current value corresponding to the minimum position, a step of picking up enlarged specimen images by changing astigmatism correction current of a stigmator in Y direction, a step of image-calculating image sharpness coefficients of the enlarged specimen images, a step of determining a minimum position sandwiched by two peaks on a curve indicative of the relation between astigmatism correction current of the stigmator in Y direction and image sharpness coefficient, and a step of setting the astigmatism correction current of the stigmator in Y direction to a current value corresponding to the minimum position.

When two peaks are determined to exist in the decision, the minimum position sandwiched by the two peaks may be determined before the astigmatism correction process proceeds and the focal position of the electron beam may be set to a position corresponding to the minimum position.

A specimen observing method based on an electron microscope according to this invention comprises a step of picking up enlarged specimen images by changing focal position of an electron beam in relation to a specimen, a step of image-calculating an angular direction component of image sharpness coefficient of the enlarged specimen image, a step of deciding an astigmatism correction direction from a result of the calculation of the angular direction component of image sharpness coefficient, a step of picking up enlarged specimen images by changing the astigmatism correction current of stigmator in the determined direction, a step of calculating image sharpness coefficients of the enlarged specimen images, a step of determining a minimum position sandwiched by two peaks on a curve indicative of the relation between astigmatism correction current of stigmator and image sharpness coefficient, and a step of setting the astigmatism correction current of the stigmator to a current value corresponding to the minimum position.

After the astigmatism correction has ended, a focus correction process proceeds. The focus correction process includes a step of picking up enlarged specimen images by changing focal position of an electron beam in relation to a specimen, a step of calculating image sharpness coefficients of the enlarged specimen images, a step of determining a peak position on a curve indicative of the relation between focal position of the electron beam and image sharpness coefficient, and a step of setting the focal position of the electron beam to a position corresponding to the peak position.

Preferably, the image sharpness coefficient may be image-calculated in respect of an edge enhanced image of the enlarged specimen image.

A specimen observing method based on an electron microscope for performing a process of making focal point of an electron beam coincident with a specimen after a process of correcting astigmatism of the electron beam according to this invention carries out a process of making focal position of the electron beam substantially coincident with the specimen before the process of correcting astigmatism of the electron beam, wherein the process of making focal position of the electron beam substantially coincident with the specimen comprises a step of picking up enlarged specimen images by changing the focal position of the electron beam in relation to the specimen, a step of calculating pixel mean values of the enlarged specimen images, a step of determining a minimum position on a curve indicative of the relation between focal position of the electron beam and pixel mean value, and a step of setting the focal position of the electron beam to a position corresponding to the minimum position, and wherein the process of correcting astigmatic aberration of the electron beam is carried out through the aforementioned steps.

A specimen observing method based on an electron microscope for performing a process of making focal point of an electron beam coincident with a specimen after a process of correcting astigmatism of the electron beam according to this invention carries out a process of making focal position of the electron beam substantially coincident with the specimen before the process of correcting astigmatism of the electron beam, wherein the process of making focal position of the electron beam substantially coincident with the specimen comprises a step of picking up enlarged specimen images by changing focal position of the electron beam in relation to the specimen, a step of calculating image sharpness coefficients of the enlarged specimen images, a step of calculating pixel mean values of the enlarged specimen images, a step of determining a ratio between the image sharpness coefficient and the pixel mean value at each focal position, a step of determining a maximum position on a curve indicative of the relation between the focal position of the electron beam and the ratio, and a step of setting the focal position of the electron beam to a position corresponding to the maximum position, and wherein the process of correcting astigmatism of the electron beam is carried out through the aforementioned steps.

Preferably, the process of making focal position of the electron beam substantially coincident with the specimen, carried out before the process of correcting astigmatism of the electron beam, may be performed at a lower magnification than a specimen observation magnification.

By determining an astigmatic difference amount from two peaks when the presence of the two peaks is determined in the decision of the number of peaks on a curve indicative of the relation between focal position of the electron beam and image sharpness coefficient, the range within which the astigmatism correction current is changed can be determined on the basis of the astigmatic difference amount. Alternatively, when the astigmatic difference amount is larger than a predetermined threshold value, the astigmatism correction process may proceed. Measurement of the astigmatic difference amount and the astigmatism correction process may be repeated until the astigmatic difference amount becomes smaller than the threshold value.

According to the present invention, by automating the astigmatism correction, conventionally carried out manually, in combination with the focus correction, the operator can be allowed for obtaining an image of a quantitatively given astigmatic difference amount with high reproducibility without resort to knowing status of astigmatism and focus and operational capability of the electron microscope can be improved.

Other objects, features and advantages of the invention will become apparent from the following description of the embodiments of the invention taken in conjunction with the accompanying drawings.

BRIEF DESCRIPTION OF THE DRAWINGS

FIG. 9A is a diagram showing the relation between X-direction stigmator coil current value and angle dependent image sharpness coefficient on the over-focus side.

FIG. 9B is a diagram showing the relation between X-direction stigmator coil current value and angle dependent image sharpness coefficient on the under-focus side.

FIG. 9C is a graph showing examples of angle dependent image sharpness coefficient components of X-direction astigmatism in relation to stigmator current coil current on the over-focus side.

FIG. 17 is a flowchart of a process for preventing erroneous operation by adding a pixel mean value calculation process.

DESCRIPTION OF THE EMBODIMENTS

Embodiments of the present invention will now be described by way of example with reference to the accompanying drawings.

Figure 1:
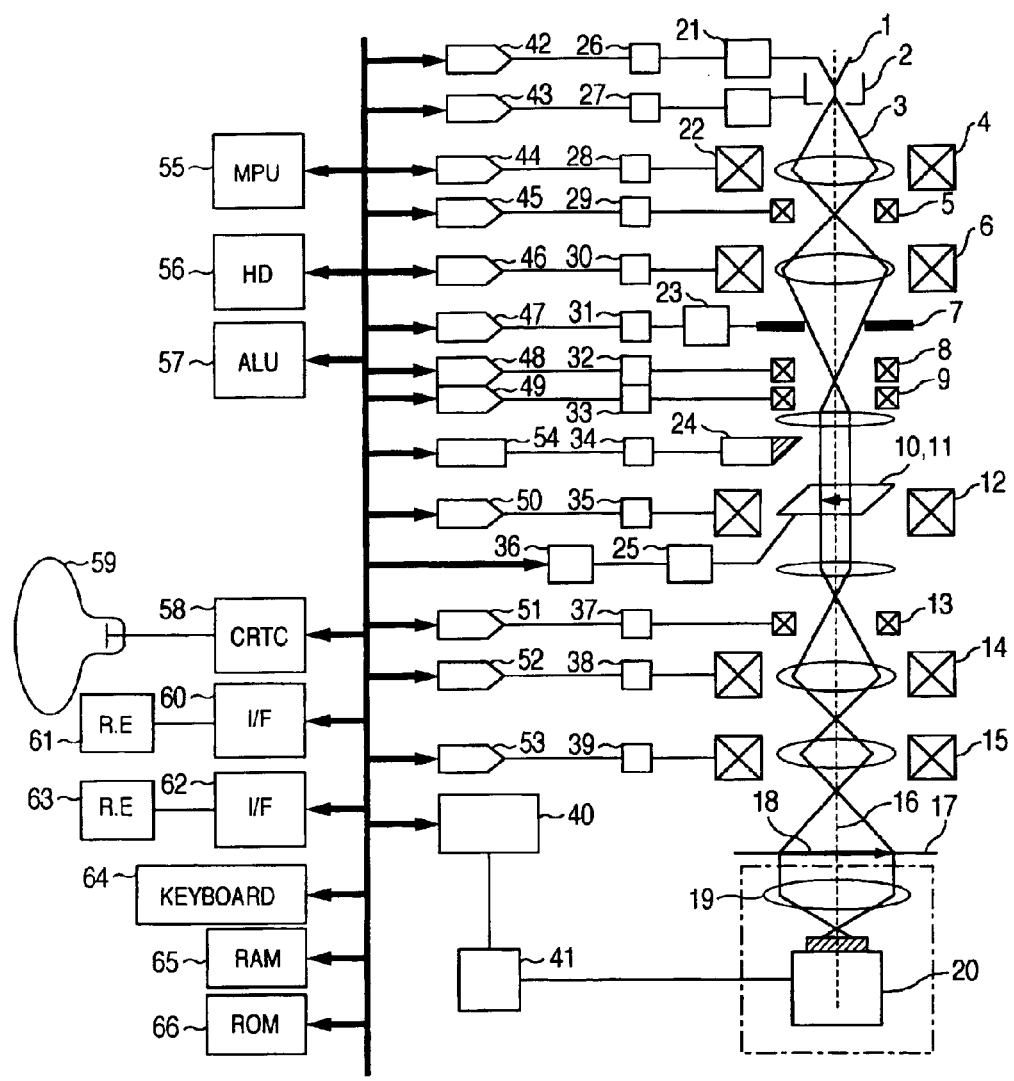
FIG. 1 is a functional block diagram showing the construction of an electron microscope of the present invention.

Referring first to FIG. 1, there is illustrated, in schematic functional block diagram form, an example of an electron microscope according to this invention. In the present invention, the number of stages of electron beam deflection coils does not matter and in this embodiment, one stage is provided upwardly of a specimen and the other stage is provided downwardly of an objective lens. Also, in this invention, the number of illumination lens systems does not matter and in the present embodiment, two stages are provided. Further, the number of projection lens systems is arbitrary and in this embodiment, a two-stage lens system is employed.

An electron beam 3 emitted from an electron beam source 1 and then accelerated travels through a first condenser lens coil 4, a second condenser lens coil 6 and a pre-magnetic field of objective lens coil 12 so as to be irradiated on a specimen 11 held by a specimen stage 10. The electron beam 3 may be deflected by means of a scan coil 9 so as to be scanned on the specimen. The electron beam 3 transmitting through the specimen is enlarged by means of a post magnetic field of objective lens coil 12, an intermediate lens coil 14 and a projection lens coil 15, so that an enlarged specimen image 18 can be formed on a fluorescence screen 17. The enlarged specimen image 18 of the electron beam 3 transmitting through the specimen 11, thus formed on the fluorescence screen 17, is converted into light which in turn is enlarged or reduced through the medium of an optical lens 19 and is converted into a video signal current by means of an image capturing device 20. The video signal current of the image capturing device 20 is fetched, through an image fetch driver 41 and an image capturing device controller 40, by means of a microprocessor 55 and processed thereby and thereafter an image is displayed on an image display unit 59 controlled by an image display unit controller 58.

In the present embodiment, the enlarged specimen image 18 of the electron beam transmitting through the specimen is converted into a video signal current by using the image capturing unit comprised of the fluorescence screen 17, optical lens 19 and image capturing device 20 but alternatively, it may be converted into a signal current by using, for example, a micro channel plate (MCP) capable of directly converting the electron beam into a video signal current. In case the specimen 11 is scanned with the electron beam by using the scan coil 9, secondary electrons or scattered electrons emanating from the specimen 11 may be detected by means of an electron detector 24 comprised of a photo-electron multiplier or MCP and an enlarged specimen image can be obtained on the basis of a detection signal of the electron detector. The detection signal of electron detector 24 is fetched by the microprocessor 55 through a small current amplifier 34 and a current detection controller 54. In the microprocessor 55, an image signal composed of the scan signal and detection signal is formed in synchronism with scan control of the electron beam 3 and an enlarged specimen image is displayed on the image display unit 59 through the image display controller 58.

The image signal displayed on the image display unit 59 is saved in an external memory unit 56 or a random access memory 65.

The microprocessor 55 controls, through digital/analog converters (DAC's) 44, 46, 50, 52 and 53, excitation power supplies 28, 30, 35, 38 and 39 for feeding the first condenser lens coil 4, second condenser lens coil 6, objective lens coil 12, intermediate lens coil 14 and projection lens coil 15 of the electron microscope. The microprocessor 55 also controls, through DAC's 45, 48, 49 and 51, excitation power supplies 29, 32, 33 and 37 for feeding the stigmator coil 5, electron beam deflection coil 8, electron beam scan coil 9 and electron beam deflection coil below specimen 13.

Coupled to the microprocessor 55 are the external memory unit 56 such as hard disk or magneto optic recording unit, arithmetic logic unit 57, image display unit controller 58, image display unit 59, keyboard 64, random access memory (RAM) 65 and read only memory (ROM) 66. A magnification switching rotary encoder 61 and a specimen stage movement operation rotary encoder 63 are coupled to the microprocessor 55 through interfaces (I/F's) 60 and 62, respectively.

An aperture 7 is driven by means of driving power supplies 31 and 23 coupled to the microcomputer 55 through a DAC 47. The specimen stage 10 is driven by means of a driver 25 for specimen stage driving coupled to the microprocessor 55 through a driving circuit 36.

Next, to exemplify image calculation in the present invention, the principle of determining an image sharpness coefficient by means of an image filter and the principle of auto focusing and auto astigmatism correction will be described.

Figure 3A:
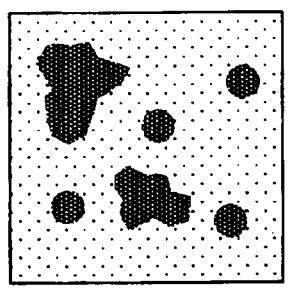
FIG. 3A is a diagram showing contrast of an image to explain image sharpness coefficient.
Figure 3B:
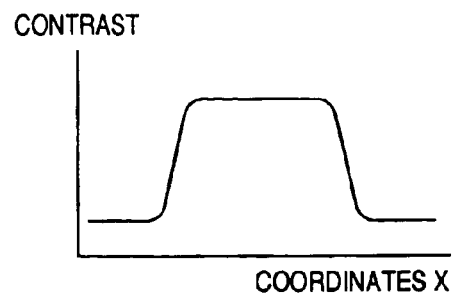
FIG. 3B is a graph showing a line profile in the FIG. 3A image.
Figure 3C:
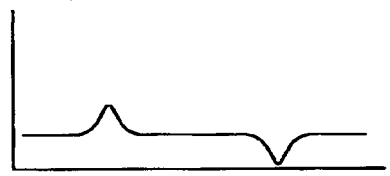
FIG. 3C is a graph showing a first order differential of the line profile.

An example of a manner of determining an image sharpness coefficient will first be described. An enlarged specimen image of an arbitrary specimen as shown in FIG. 3A is recorded with M×N pixels in the memory unit. This two-dimensional image is expressed by a functional form f(i,j). A specimen structure portion contained in the original image of FIG. 3A is depicted in the form of a contrast line profile along image coordinates x as shown in FIG. 3B. A first order differential image of this image can be obtained as a contrast line profile as shown in FIG. 3C. Namely, the first order differential image of the two-dimensional image is expressed by equation (1) by using vector operator nabla.

$$\nabla f(x, y) = \frac{\partial f(x, y)}{\partial x} + \frac{\partial f(x, y)}{\partial y} \qquad (1)$$
$$= f_x(x, y) + f_y(x, y)$$

where $f_x(x,y)$ and $f_y(x,y)$ represent first order differentials in x and y directions, respectively. When being generalized to digital images, equation (1) corresponds to the difference. Where first order differentials in x and y directions of the image f(i,j) are represented by fx(i,j) and fy(i,j), they are expressed by equation (1.2).

$$f_x(i,j) = f(i+1,j) - f(i,j)$$
$$f_y(i,j) = f(i,j+1) - f(i,j) \qquad (1.2)$$

Namely, the difference in x direction is calculated using two pixels which are mutually adjacent in x direction and the difference in y direction is calculated using two pixels which are mutually adjacent in y direction.

Figure 3D:
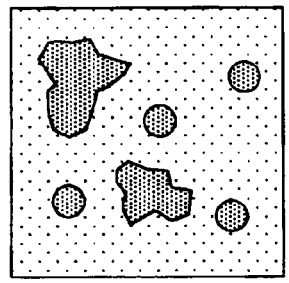
FIG. 3D is a graph showing a second order differential of the line profile.
Figure 3E:
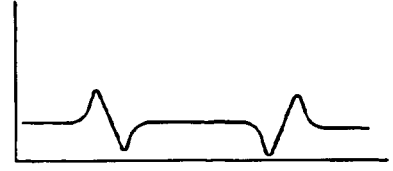
FIG. 3E is a diagram showing an edge enhanced image of the FIG. 3A image.

Subsequently, the original image is subjected to a second order differential to provide an image of contrast line profile as shown in FIG. 3E. For an analog image, the second order differential image is expressed by equation (2) by using vector operator Laplacian.

$$\nabla^2 f(x, y) = \frac{\partial f^2(x, y)}{\partial x} + \frac{\partial f^2(x, y)}{\partial y} \qquad (2)$$
$$= f_{xx}(x, y) + f_{yy}(x, y)$$

When the above is generalized to two-dimensional digital images, equation (2) can be indicated in a difference form similarly to the case of the first order differential. For example, on the assumption that there is a series of pixels such as [D] [A] [B], a pixel of [A] is noticed at present. Then, the differences are calculated between pixels A and D and between pixels B and A. The differences are expressed by equation (3).

$$f_x(A-D) = f(i,j) - f(i-1,j)$$
$$f_x(B-A) = f(i+1,j) - f(i,j) \qquad (3)$$

Through this operation, first order differentials which are shifted by 0.5 pixels to the left and right (horizontally) from the pixel A can be obtained. In Y direction, too, first order differentials which are shifted vertically by 0.5 pixels can be obtained. Next, the difference is again calculated between $f_x(A-D)$ and $f_y(B-A)$ to perform an operation for obtaining a second order differential in respect of the noticed pixel A.

$$f_{xx}(i, j) = f_x(B-A) - f_x(A-D) \qquad (4.1)$$
$$= \{f(i+1, j) - f(i, j)\} - \{f(i, j) - f(i-1, j)\}$$
$$= f(i-1, j) - 2f(i, j) + f(i+1, j)$$

$$f_{yy}(i, j) = f(i, j-1) - 2f(i, j) + f(i, j+1) \qquad (4.2)$$

By substituting equations (4.1) and (4.2) to equation (2) and linearly combining $f_{xx}(i,j)$ and $f_{yy}(i,j)$, the second order differential of the digital image f(i,j) can be expressed by equation (5).

$$\nabla^2 f(i, j) = f_{xx}(i, j) + f_{yy}(i, j) \qquad (5)$$
$$= \{f(i-1, j) - 2f(i, j) + f(i+1, j)\} +$$
$$\{f(i, j-1) - 2f(i, j) + f(i, j+1)\}$$
$$= f(i, j-1) + f(i-1, j) - 4f(i, j) + f(i+1, j) + f(i, j+1)$$

A weight coefficient h for the first order differential of equation (3) and for the second order differential of equation (5) is expressed in the form of matrixes by the following equation.

$$h_x = \begin{bmatrix} -1 & 1 \\ 0 & 0 \end{bmatrix} \qquad (6)$$
$$h_y = \begin{bmatrix} -1 & 0 \\ 1 & 0 \end{bmatrix}$$

By using equation (6), the first order differential of equation (1.2) can be indicated through calculation as below.

$$f_x(i, j) = \sum_{k=0}^{1}\sum_{l=0}^{1} f(i+k, j+l)h_x(k, l) \qquad (7.1)$$

$$f_y(i, j) = \sum_{k=0}^{1}\sum_{l=0}^{1} f(i+k, j+l)h_y(k, l) \qquad (7.2)$$

In the weight coefficient h, the coefficient can be given not only in x and y directions as indicated by equation (6) but also diagonally. The form generalized in angular components can be given by equation (7.3).

$$f_\theta(i, j) = \sum_{k=0}^{1}\sum_{l=0}^{1} f(i+k, j+l)h_\theta(k, l) \qquad (7.3)$$

A weight coefficient $h_{(45)}$ given diagonally in 45° direction and a weight coefficient $h_{(135)}$ given diagonally in 135° direction can be expressed by equation (8).

$$h_{(45)} = \begin{bmatrix} 0 & 1 \\ -1 & 0 \end{bmatrix} \qquad (8)$$
$$h_{(135)} = \begin{bmatrix} 1 & 0 \\ 0 & -1 \end{bmatrix}$$

In performing the differential process of images, there is available a weight coefficient which gives the averaging effect in order to suppress extraction of noise to as small a level as possible. For example, in a coefficient called Sobel coefficient which is expressed by equation (9), weighting is applied to upper, lower, left and right pixels, 9 pixels in total, to cope with noise.

$$h_x = \begin{bmatrix} -1 & 0 & 1 \\ -2 & 0 & 2 \\ -1 & 0 & 1 \end{bmatrix} \qquad (9)$$

-continued $$h_y = \begin{bmatrix} -1 & -2 & -1 \\ 0 & 0 & 0 \\ 1 & 2 & 1 \end{bmatrix}$$

A method of determining an image sharpness coefficient according to the present embodiment is exemplified as below. First order differentials of an original image are determined in x and y directions, respectively. In this phase, by taking noise reduction into account, noise considered type weight coefficients as shown in FIG. 9 are multiplied. By performing subtraction between the original image and the first order differentials, edge enhanced images Gx and Gy are determined in x and y directions, respectively. An example of edge enhanced images is shown in FIG. 3D.

An absolute value G of the edge enhanced images is given by the following equation.

$$G(x, y) = |G_x + G_y| \qquad (10)$$
$$= \sqrt{(G_x^2 + G_y^2)}$$

Where a mean value of edge enhanced images G over M×N pixels is indicated by Gavg, this mean value is given by equation (11).

$$G_{avg} = \frac{\sum_x \sum_y G(x, y)}{M \times N} \qquad (11)$$

A dispersion determined from equations (10) 5 and (11) indicates an image sharpness coefficient of the original image.

$$V = \frac{\sum_x \sum_y \{G(x, y) - G_{avg}\}^2}{M \times N} \qquad (12)$$

Further, the image sharpness coefficient can also be determined in the form of a standard deviation.

$$\sigma = \sqrt{V} \qquad (13)$$
$$= \sqrt{\frac{\sum_x \sum_y \{G(x, y) - G_{avg}\}^2}{M \times N}}$$

The image sharpness coefficient can be decomposed into directional components. For example, an image sharpness coefficient in x direction and an image sharpness coefficient in 45° direction are available. For example, when the Sobel weighting coefficient is used, directional components can be obtained 45° stepwise by weight coefficients as indicated in the following equation.

0° (x) component $$h_{(0)} = \frac{1}{4} \begin{bmatrix} -1 & 0 & 1 \\ -2 & 0 & 2 \\ -1 & 0 & 1 \end{bmatrix} \qquad (14.1)$$

45° component $$h_{(45)} = \frac{1}{3} \begin{bmatrix} -1 & -1 & 0 \\ -1 & 0 & 1 \\ 0 & 1 & 1 \end{bmatrix} \qquad (14.2)$$

90°(y) component $$h_{90} = \frac{1}{4} \begin{bmatrix} -1 & -2 & -1 \\ 0 & 0 & 0 \\ 1 & 2 & 1 \end{bmatrix} \qquad (14.3)$$

135° component $$h_{(133)} = \frac{1}{3} \begin{bmatrix} 0 & -1 & -1 \\ 1 & 0 & -1 \\ 1 & 1 & 0 \end{bmatrix} \qquad (14.4)$$

By using the weight coefficients as above, differentials at angles in 4 directions are determined, edge enhance images in the individual directions are calculated and an angular component of image sharpness coefficient can be obtained from a dispersion or standard deviation of each sole component.

Figure 4A:
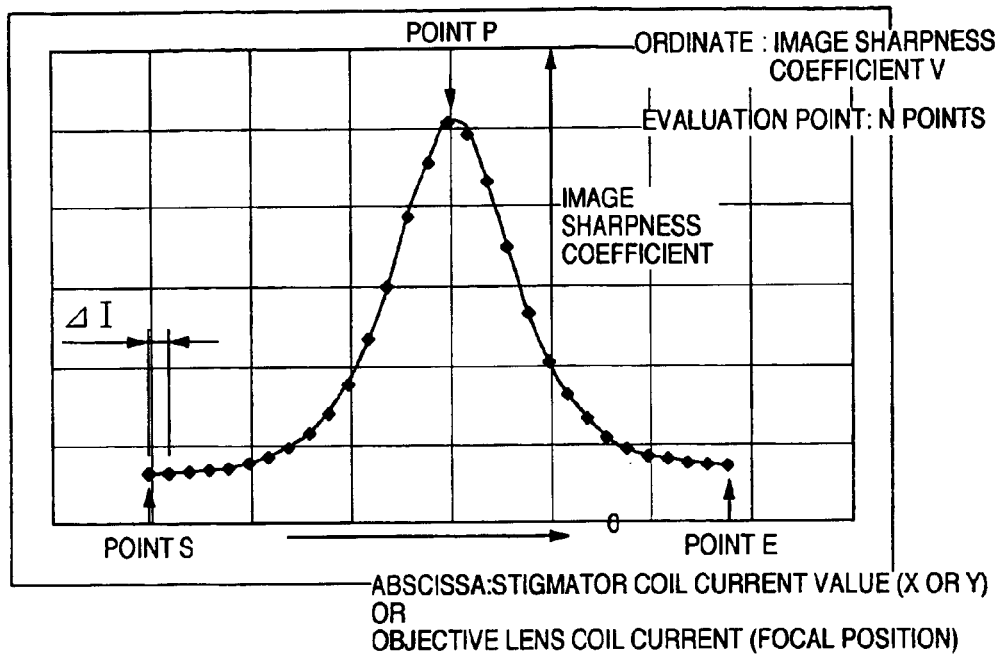
FIG. 4A is a graph showing the relation between stigmator coil current or objective lens coil current and image sharpness coefficient in the absence of astigmatism.

Next, a process for making focus correction by using the image sharpness coefficient will be described. When the focal position is changed in respect of an image of a specimen, the focal positions are related to image sharpness coefficients as shown in FIG. 4A. In the figure, abscissa represents objective lens coil current values defining focal positions and ordinate represents image sharpness coefficients indicated by equation (13) (specifically, representing the square sum of squared image sharpness coefficients of 0°, 45°, 90° and 135° components).

Figure 2:
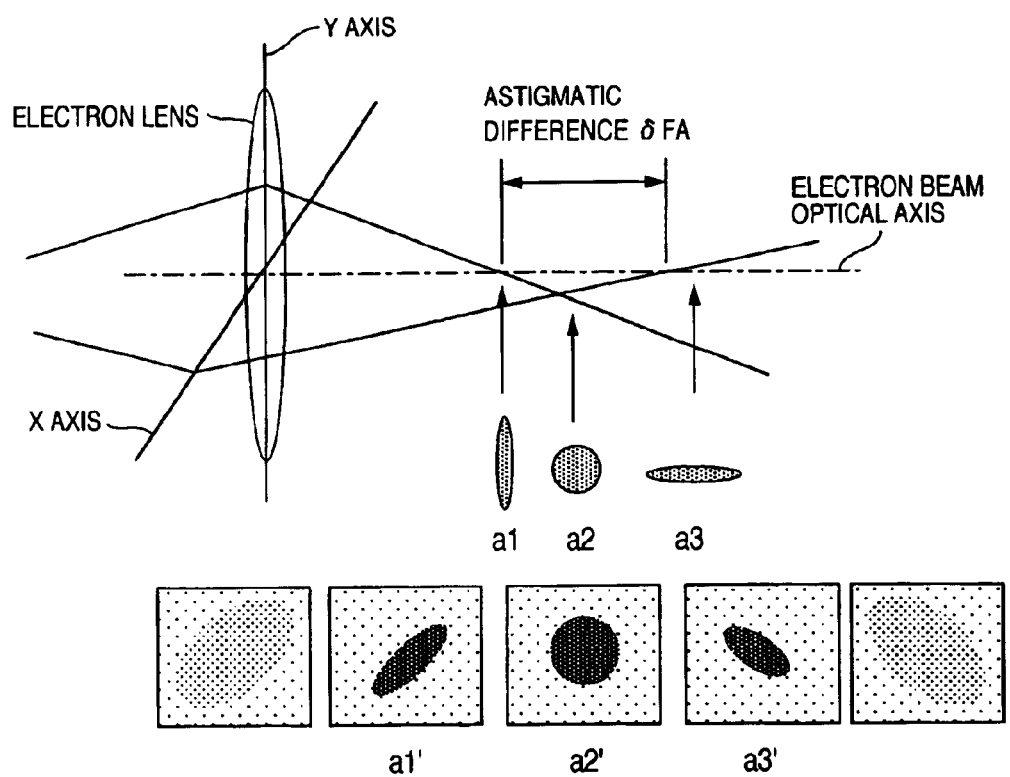
FIG. 2 is a diagram useful to explain generation of astigmatism of an electron lens and an enlarged specimen image.

In this graph, the objective lens coil current is changed stepwise by a step width of ΔI starting from a point S to change the focal position and image sharpness coefficients of the image are measured at individual focal positions so as to search an exact focus position. In the process of performing focus correction, a method is employed in which the focal position is changed and an image sharpness coefficient at each focal position is evaluated. The number of evaluation points is N (in the figure, 30 points). Generally, the exact focus position exists at a site where a least circle of confusion as shown at a2 in FIG. 2 is formed. The focal position is in direct proportion to excitation current I of the objective lens coil. The exact focal position is a position where the electron beam forms a least circle of confusion to form the sharpest image and this position is indicated by P point in FIG. 4A. As will be seen from this graph, a decision is made such that the P point at which the image sharpness coefficient is the highest corresponds to the exact focal position. On the assumption that no astigmatism exists, the FIG. 4A example is given and in such a case, only one peak corresponding to the P point occurs when the focus is changed.

Even when in FIG. 4A the abscissa substitutes the focal position for stigmator current values, a similar image sharpness coefficient curve can be obtained. If abscissa represents sigmator currents in FIG. 4A, the P point where the image sharpness coefficient is the highest corresponds to an optimum astigmatism correction value and the P point alone occurs only when the focal position is at an exact focus.

In FIG. 2, when the distance between a1 and a3 on the electron beam optical axis is δfa, this δfa represents an astigmatic difference. More particularly, because of asymmetry of lens intensities in x-axis and y-axis directions in the electron optical system, focal positions in the x-axis and y-axis directions are at a3 and a1, respectively, and the distance therebetween corresponds to the astigmatic difference δfa. On the other hand, in the absence of any astigmatic aberration, that is, with the symmetry of the electron optical system maintained, a spot of least circle of confusion is formed at a2 where the focal positions in the x-axis and y-axis directions coincide with each other and a formed image can have the highest image sharpness coefficient. At that time, the astigmatic difference becomes zero. With the astigmatic difference nullified, the number of peaks is only one in FIG. 4A.

In the presence of astigmatism, the focal position is related to the image sharpness coefficient as will be described below with reference to FIG. 4B. As in the case of FIG. 4A, abscissa represents focal positions (objective lens coil excitation current values) and ordinate represents image sharpness coefficients (representing the square sum of squared image sharpness coefficients of 0°, 45°, 90° and 135° components). In the presence of astigmatism, two peaks develop at P1 point and P2 point as shown in the figure. This is because a directional component of image is elongated as shown at a1' or a3' in FIG. 2 and only an edge in one direction is detected. In this case, an exact focal position exists at a position corresponding to a valley indicated at B point between the two peaks. With the astigmatism, the asymmetry of the electron optical system causes x-axis and y-axis focal positions to develop at the different positions a3 and a1, respectively, and the two peaks take place on the image sharpness coefficient curve. The astigmatic difference δfa corresponds to the distance between the two peaks.

It should be understood that where abscissa represents stigmator coil lens current values and ordinate represents image sharpness coefficients (the square sum of squared image sharpness coefficients of 0°, 45°, 90° and 135° components), the presence of the two peaks at P1 and P2 points shows that the focus deviates from the exact focal position.

Figure 5:
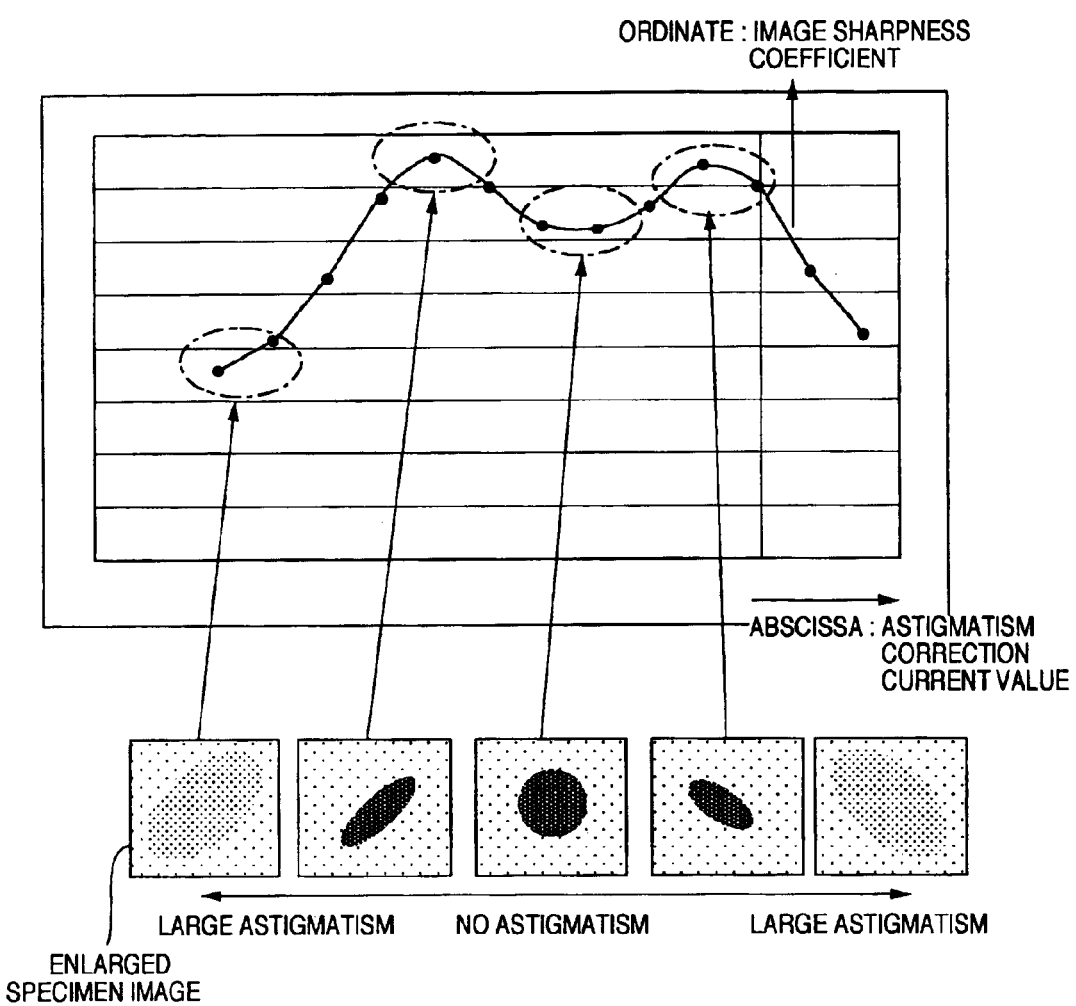
FIG. 5 is a diagram showing the relation among stigmator coil current, image sharpness coefficient and enlarged specimen image.

The astigmatism correction current value, image sharpness coefficient and enlarged specimen image are diagrammatically illustrated in FIG. 5. It is now assumed that an enlarged specimen image in a view field noticed at present has circular image contrast. In the absence of any astigmatic aberration, the enlarged specimen image exhibits a circular image but in the presence of an astigmatic aberration, the specimen transmitting enlarged image exhibits an elongated image as illustrated. As the astigmatic aberration becomes very large to degrade the image sharpness coefficient remarkably, the image contrast of the enlarged specimen image lowers.

By making reference to a flowchart in FIG. 6, a first embodiment of the present invention will be described. In the present embodiment, the electron microscope shown in FIG. 1 is used to decide whether the focus of an enlarged specimen image is defocused and at the same time whether astigmatism exists and to perform automatic correction, thereby solving the first problem.

In step S101, the use of the electron microscope is started. A desired specimen 11 is mounted to the specimen stage 10 and is then inserted to the electron microscope. In step 102, a desired magnification is set by means of the magnification switching rotary encoder 61 shown in FIG. 1. Concurrently, data of electron beam source precedently recorded in the ROM 66 is called out and processed by the microprocessor 55 so that a current may be delivered out of a DAC 42 and a stabilizer 26. This current is supplied to the emitter 1 via a cathode power supply 21 and electrons are emitted from the emitter 1. As for acceleration voltage, data is called out of the ROM 66 and processed by the microprocessor 55 and current is delivered out of a DAC 24 and a stabilizer 27. This current is boosted by a high voltage power supply 22 and applied to an acceleration electrode 2, with the result that an electron beam 3 emitted from the emitter 1 can be accelerated by a high voltage applied to the acceleration electrode 2. The respective lens coils of first condenser lens coil 4, second condenser lens coil 6, objective lens coil 12, intermediate lens coil 14 and projection lens coil 15 are applied with lens currents from the DAC's and lens coil excitation power supplies on the basis of lens coil data recorded on the ROM 66 in advance. The respective coils of stigmator coil 5, deflection coil 8, electron beam scan coil 9 and deflection coil below specimen 13 are applied with coil currents from the DAC's and coil excitation power supplies in accordance with coil data recorded on the ROM 66 in advance. In the step S102, focus correction parameters and astigmatism correction parameters are also called out of the ROM 66.

Figure 7:
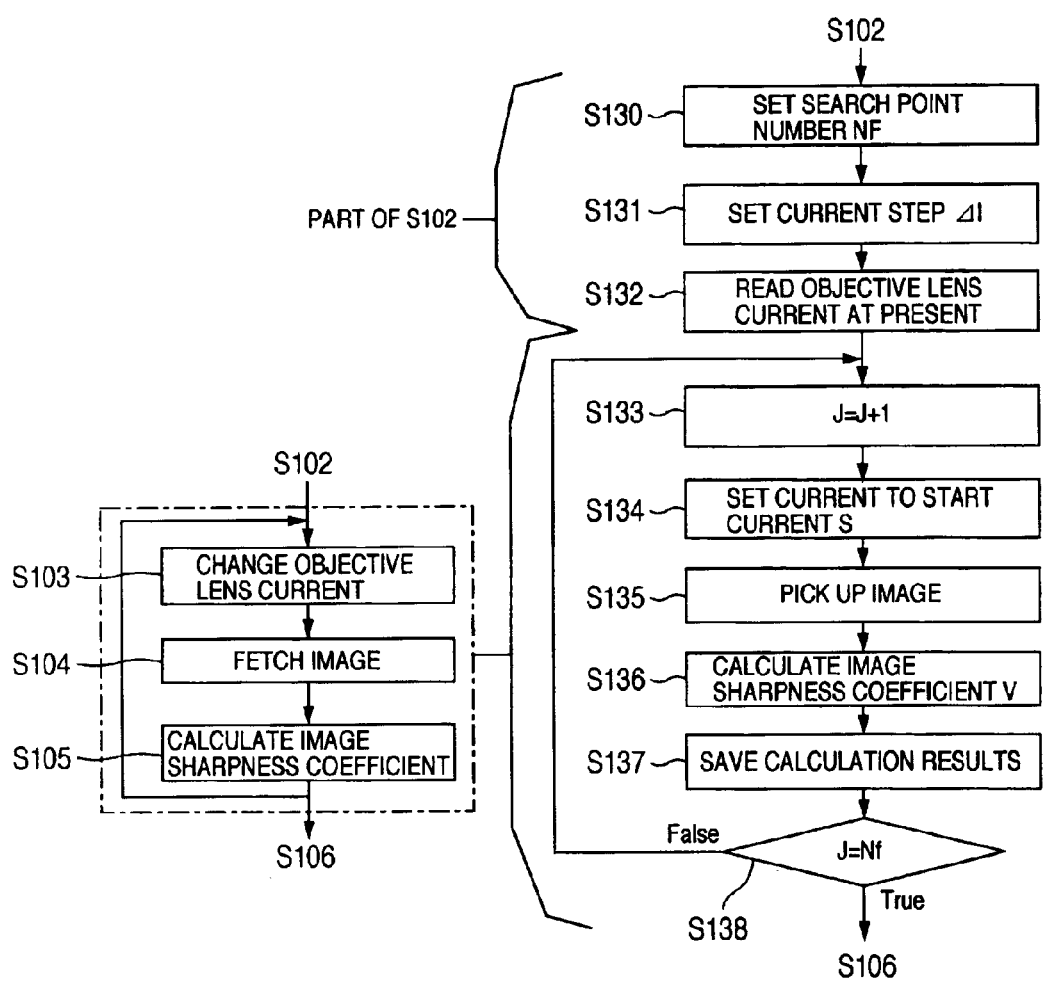
FIG. 7 is a flowchart for explaining part of the FIG. 6 flowchart.

In steps S103 through S105, images are fetched by changing the focal position and the image sharpness coefficient is calculated every fetching operation. With reference to FIG. 7, an example of a process over the steps S102 to S105 will be described. After the initial setting has been completed in the step S102, a search point number Nf is set in step S130. For this setting, data registered in the ROM in advance may be called out or data may be inputted by the operator. The search point number Nf corresponds to the evaluation point number N in FIG. 4. In step S131, a current step ΔI is called out of the ROM. This ΔI has relation to accuracy of focus correction value based on the image sharpness coefficient. With the current step ΔI set to a large value, the accuracy is degraded but operation time can be shortened. On the other hand, with the current step ΔI set to a small value, the accuracy can be improved. In step S132, an objective lens current value at present is called out of the microprocessor. Alternatively, the steps S130 through S132 may be executed as part of the initial setting in the step S102.

By using the objective lens current value at present obtained in the step S132 as a reference, a start current S is set in step S134. The start current S is calculated from the objective lens current value at present, search point number Nf and current step ΔI. For example, an objective lens current having a smaller value than the objective lens current at present is set as the start current S. Firstly, in step S135, a specimen enlarged image at the start current S is captured and saved in the RAM 65. Next, in step S136, an image sharpness coefficient of the enlarged specimen image is calculated by means of the ALU 57. For calculation of the image sharpness coefficient, equation (12) or equation (13) without directional dependency is used. The thus calculated image sharpness coefficient is related to the objective lens current value and saved in the RAM in step S137. In step 138, the number incremented in step S133 is counted and a series of steps S134 to S137 of the current setting, capturing, image sharpness coefficient calculation and calculation result save are repeated until the search point number Nf is reached. In the above description, the focal position is changed by changing the objective lens coil current but alternatively, the focal position may be changed by changing the specimen height by means of a height drive 23 of specimen stage 10.

Reference is made again to FIG. 6. By repeating the steps S103 through S105, a curve as shown in FIG. 4A or 4B is obtained depending on the relation between current value and image sharpness coefficient. In step S106, it is decided whether the peak number Np is one or two. If Np=1 stands, no stigmatic aberration is determined and the program proceeds to step S115 but if Np=2 stands, the presence of astigmatism is determined and the program proceeds to step S107.

In the step S107 to step S110, astigmatism correction current in X direction is changed, an enlarged specimen image is captured and an image sharpness coefficient V is calculated. From the relation between astigmatism correction current and image sharpness coefficient, a bottom position corresponding to B point in FIG. 4B is searched. An X stigmator coil current corresponding to the searched bottom position B point is adjusted to remove an astigmatic aberration in X direction.

In steps S111 through S114, an operation similar to that in the steps S107 to S110 is applied to an astigmatic aberration in Y direction to remove it.

Figure 8:
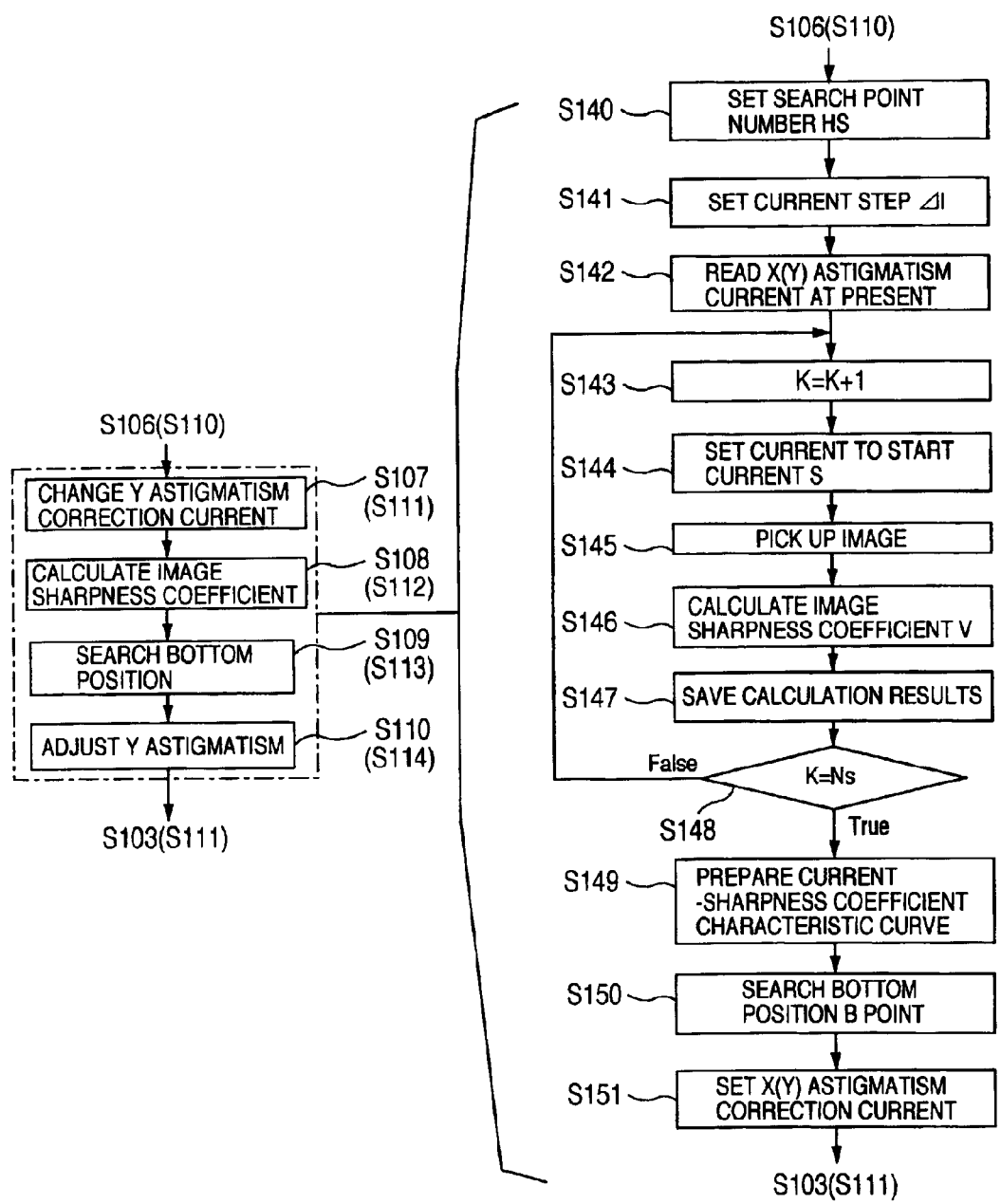
FIG. 8 is a flowchart for explaining part of the FIG. 6 flowchart.

A detailed example of operation in the steps S107 to S110 concerning the X-direction astigmatism and a detailed example of operation in the steps S111 to S114 concerning the Y-direction astigmatism will be described with reference to FIG. 8. A flowchart in FIG. 8 is for explaining an astigmatism correction method. For example, in the case of correction of an astigmatic aberration in X direction, after Np=2 has been determined to indicate the presence of an astigmatic aberration in the step S106, a search point number Ns is set in step S140. In step S141, an astigmatism correction current step A1 is set. In step S142, a current value of stigmator coil at present is called. The steps S140 to S142 correspond to initial setting for performing the astigmatism correction. Subsequently, in step S144, current is set to a current S at which an astigmatism search is started. Like the start current S explained in connection with the step S134 in FIG. 7, the start current S herein can be calculated from the stigmator coil current value at present, search point number Ns and current step A1. In step S145, an enlarged specimen image at the start current S is picked up and in step S146, an image sharpness coefficient V is calculated. For calculation of the image sharpness coefficient V, equation (12) or (13) without evaluation directivity is used. The thus calculated image sharpness coefficient V is related to the current value of stigmator coil current and is saved in the RAM in step S147. In step S148, the number incremented in step S143 is counted and a series of the steps S144 to 147 of stigmator coil current setting, capturing, image sharpness coefficient calculation and calculation result save are repeated until the search point number Ns is reached.

Figure 4B:
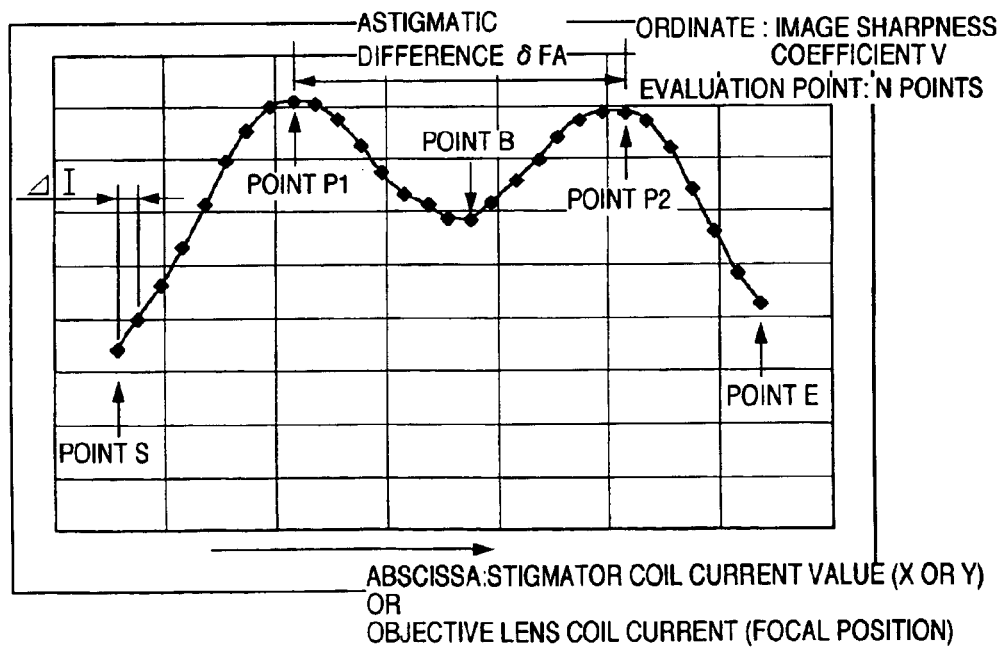
FIG. 4B is a graph showing the relation between stigmator coil current or objective lens coil current and image sharpness coefficient in the presence of astigmatism.

Further, in step S149, a curve indicative of the stigmator coil current and the image sharpness coefficient is formed and in step S150, a bottom position corresponding to the B point in FIG. 4B is searched. In step S151, a correction amount is calculated from the bottom position and the stigmator coil current value at present, and the processor transmits and applies a process to the stigmator coil so that a current may be delivered through the DAC and stigmator lens coil excitation power supply. In this manner, the astigmatism correction is carried out and the program proceeds to the next processing step S103. Here, algorithm has been described such that the stigmatism in X direction is first corrected and then the stigmatism in Y direction is corrected but Y-direction correction may otherwise be first in order of start of correction.

After the astigmatism correction has been completed in both the X and Y directions at the termination of the step S144, the program returns to the step S103 in order to calculate image sharpness coefficients by changing objective lens current and decide the number of peaks so as to decide whether an image devoid of astigmatism is obtained and whether focusing is exact. If in step S106 Np=1 is determined to conclude no astigmatism, the program proceeds to step S115. If Np=2 is determined to conclude the presence of astigmatism, the astigmatism correction routine of steps S107 to S114 is again executed.

In the step S115, a peak position corresponding to the P point in FIG. 4A is searched from the curve indicative of the image sharpness coefficient and objective lens current value calculated in the steps S103 through S105. In step S116, the peak position is compared with the objective lens coil current value at present and the current value is adjusted to an objective lens current value corresponding to the peak position to make correction to the exact focus. Through a series of operations as above, an image at exact focus removed of astigmatism can be obtained and the operation ends in step S117.

Figure 11:
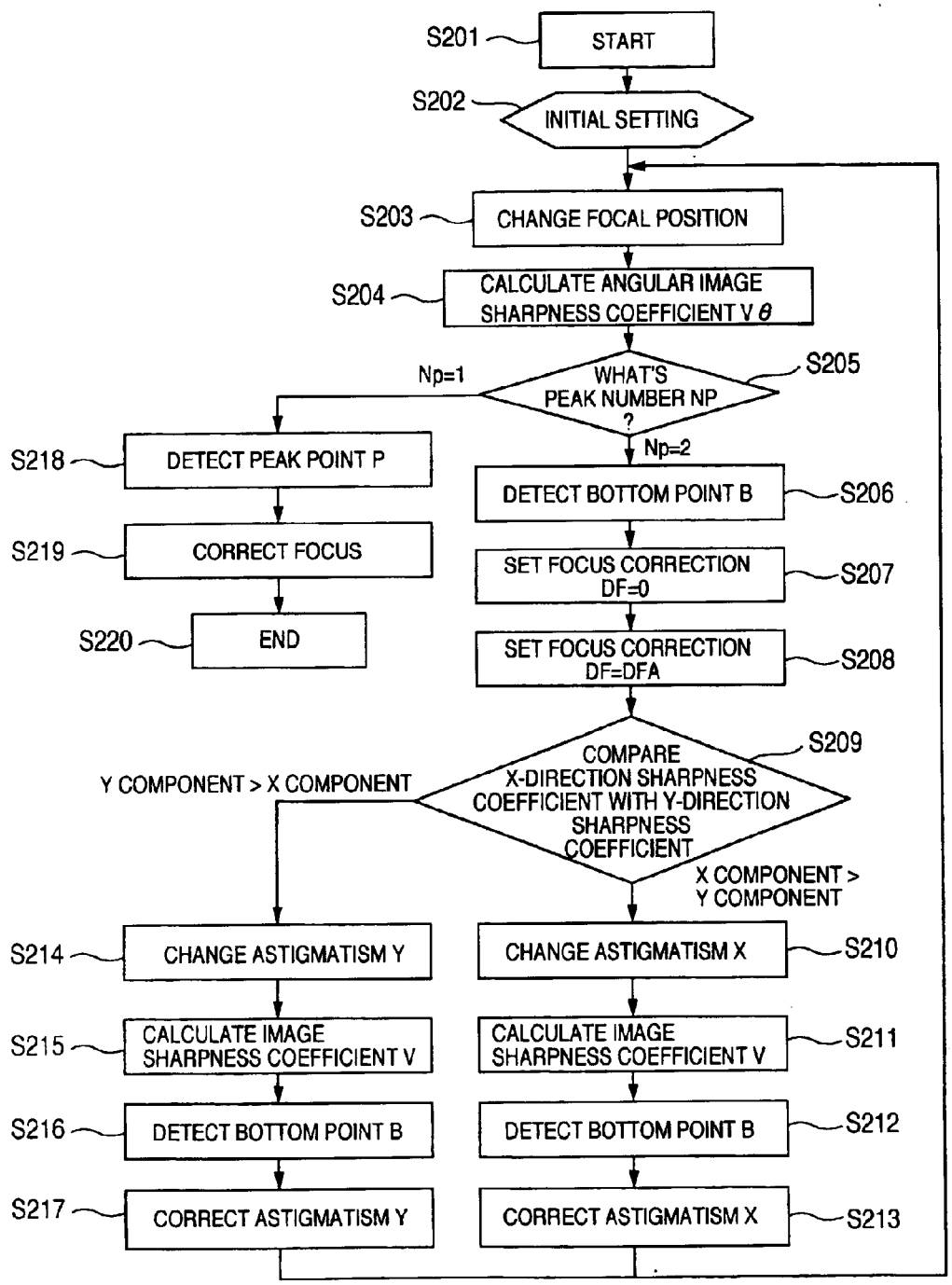
FIG. 11 is a flowchart of a process for automatically performing focus correction and astigmatism correction by using angle dependent image sharpness coefficients.

Referring now to a flowchart in FIG. 11, a second embodiment of this invention will be described. The present embodiment makes a decision as to whether the focus of an enlarged specimen image is defocused and as to whether an astigmatic aberration exists so as to perform automatic correction, thereby solving the first problem. The flowchart in FIG. 11 shows algorithm capable of determining an image sharpness coefficient dependent on angular directions with a view to simplifying algorithm and speeding up operation.

In step 201, the use of the electron microscope is started. A desired specimen 11 is mounted to the specimen stage 10 and is then inserted to the electron microscope. In step S202, setting of observation magnification, respective lens coil currents, respective deflection coil currents, focus correction parameters and astigmatism correction parameters is carried out. Step S202 corresponds to the step S102 explained in connection with FIG. 7.

In step S203, the focus is changed. This step corresponds to the steps S130 through S138 explained in connection with FIG. 7, with the exception that the step S136 is replaced with step S204. In the step S204, an image sharpness coefficient dependent on angular direction is determined. An image sharpness coefficient in θ direction is determined by multiplying an angle dependent weight coefficient indicated in equations (14.1) to (14.4). An edge enhanced image in the direction is indicated by $G_\theta$. A mean value of images $G_\theta$ over all pixels can be determined pursuant to equation (15).

$$G_{avg} = \frac{\sum_\theta G_\theta(x, y)}{M \times N} \quad (15)$$

By using equation (15), an image sharpness dispersion $V_\theta$ in the θ direction can be obtained from equation (16).

$$V_\theta = \frac{\sum_\theta \{G(x, y) - G_{avg}\}^2}{M \times N} \quad (16)$$

Further, an image sharpness standard deviation $\sigma_\theta$ can be obtained pursuant to equation (17).

$$\sigma = \sqrt{V} \quad (17)$$
$$= \sqrt{\frac{\sum_\theta \{G(x, y) - G_{avg}\}^2}{M \times N}}$$

Figure 10A:
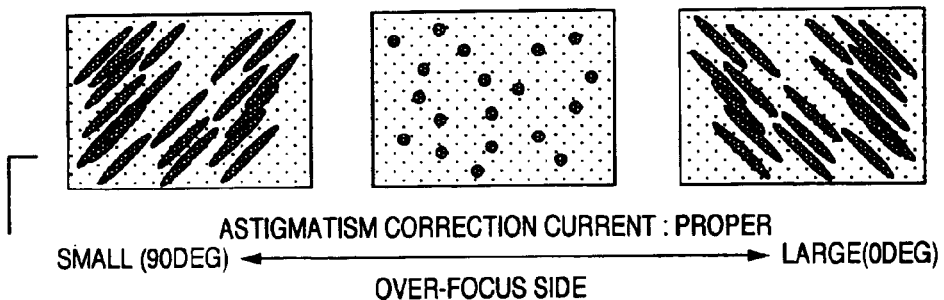
FIG. 10A is a diagram showing the relation between Y-direction stigmator coil current value and angle dependent image sharpness coefficient on the over-focus side.
Figure 10B:
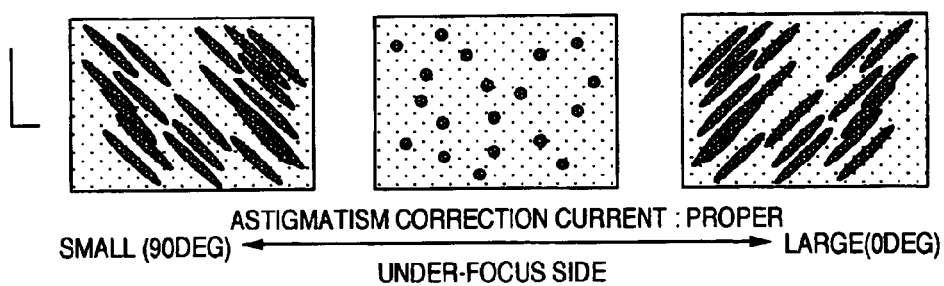
FIG. 10B is a diagram showing the relation between Y-direction stigmator coil current value and angle dependent image sharpness coefficient on the under-focus side.
Figure 10C:
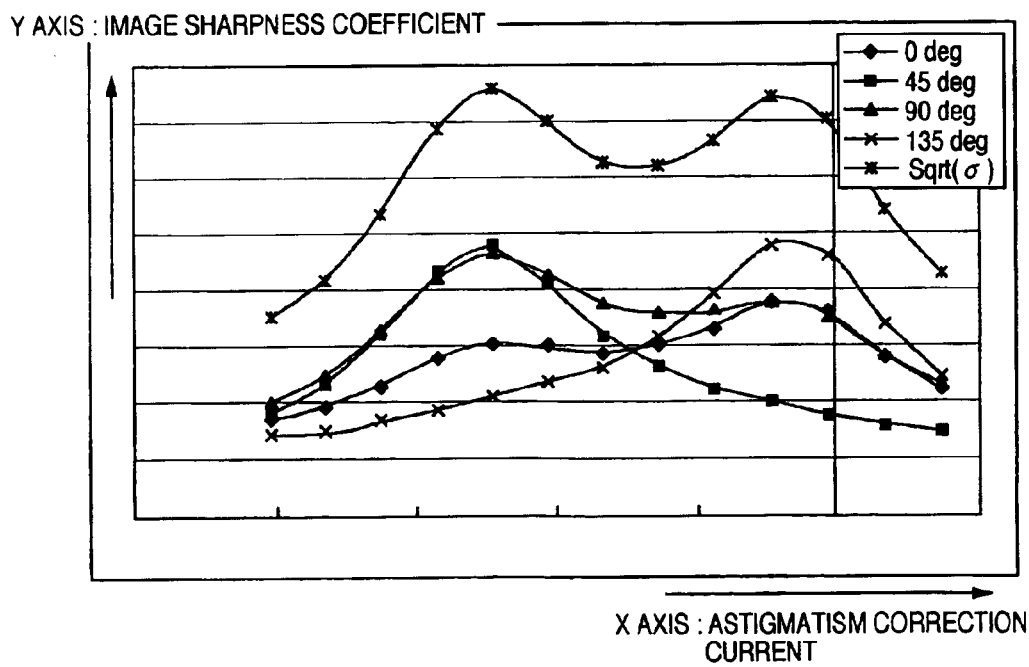
FIG. 10C is a graph showing examples of angle dependent image sharpness coefficient components of Y-direction astigmatism in relation to stigmator coil current on the over-focus side.

FIGS. 9A to 9C show the relation between correction current for astigmatism in X direction and angular component image sharpness coefficient and FIGS. 10A to 10C show the relation between correction current for astigmatism in Y direction and angular component image sharpness coefficient. When angular component dependent image sharpness coefficients of an image are considered, curves as shown in FIGS. 9C and 10C are plotted. In both FIGS. 9C and 10C, an example in the case of over-focus is illustrated.

In case the stigmator coil current is small on the overfocus side shown in FIG. 9A, the image is elongated in X direction. At that time, the image sharpness coefficient maximizes in 90° directional component as shown in FIG. 9C. In case the stigmator coil current is large, the image is elongated in Y direction and 0° directional component maximizes. On the other hand, on the under-focus side, the image is elongated in Y direction as shown in FIG. 9B and when the stigmator coil current is small, 0° directional component is maximizes. When the stigmator coil current is large, the image is elongated in X direction and 90° directional component is maximizes.

Since the Y stigmator coil has the astigmatism correction effect for the image in 45° and 135° directions, the image is elongated in both 45° and 135° directions as shown in FIGS. 10A and 10B.

By using the image elongation direction and the directional dependency of the image peak, the angle dependent image sharpness coefficient is calculated in the step S204. In step S205, a peak number Np is determined from an absolute value of angle dependent image sharpness coefficient given by equation (18).

$$V = \sqrt{V_0^2 + V_{45}^2 + V_{90}^2 + V_{135}^2} \qquad (18)$$

In equation (18), $V_0$, $V_{45}$, $V_{90}$ and $V_{135}$ represent image sharpness coefficient components at 0°, 45°, 90° and 135°. If Np=1 is determined, the absence of astigmatism in the enlarged specimen image is determined and the program proceeds to step S218. On the other hand, if Np=2 is determined, the presence of an astigmatic aberration in the enlarged specimen image is determined and the program proceeds to step S206.

In the step S206, B point corresponding to a bottom between the two peak points is detected from the profile of objective lens coil current and an absolute value of angle dependent image sharpness coefficient pursuant to equation (18). In step S207, the objective lens coil current is set to a value corresponding to the B point to bring the focus into an exact focus. In the next step S208, an objective lens coil current deviating by dfa from the objective lens coil current for the exact focus is applied to set up a focus offset intentionally.

Next, in step S209, individual angular components of the angle dependent image sharpness coefficient obtained in the step S204 are compared to each other to determine which one of sharpness coefficient components in X and Y directions is higher. If the components in 0° and 90° directions are determined to be higher, the program proceeds to step S210, in which the X-direction component is corrected. On the other hand, if the components in 45° and 135° directions are determined to be higher, the program proceeds to step S214, in which the Y-direction component is corrected.

A process in steps S210 through S213 and a process in steps S214 through S217 are quite equivalent to each other with the only exception that directions in which astigmator coil currents are applied differ and therefore, only the process in the steps S210 through S213 will be described herein. In the steps S210 to S213, operation performed in the steps S140 to S151 is carried out to correct the X-direction astigmatism. After the step S213 has been completed, the program returns to the step S203, followed by calculation of the image sharpness coefficients by changing the focal position and execution of the peak number decision step S205. If Np=1 stands and the absence of astigmatism is determined, the program proceeds to step S218.

Figure 6:
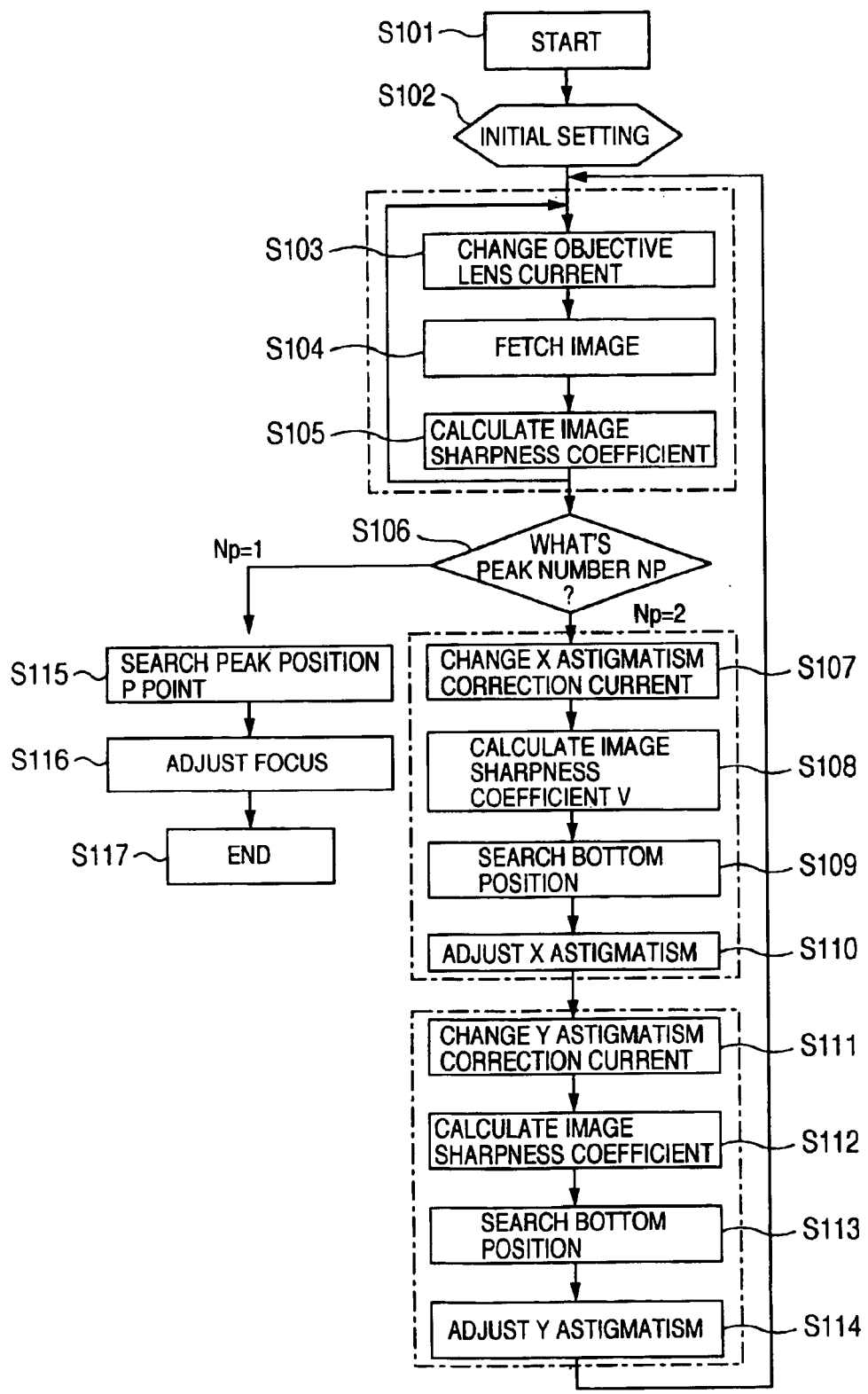
FIG. 6 is a flowchart of a process for deciding the presence or absence of an astigmatic aberration and automatically performing focus correction and astigmatism correction.

A process in steps S218 through S220 is identical to the process in the steps S115 through S117 in FIG. 6. In the step S220, an enlarged specimen image devoid of astigmatism and in exact focus can be obtained.

Referring now to a flowchart in FIG. 12, a third embodiment of this invention will be described. In this embodiment, a pixel mean value of an image is determined to capture a change in image contrast during astigmatism correction, so that under a condition that a large astigmatic aberration exists and an enlarged specimen image becomes blurred seriously, the astigmatism correction can be effected, thereby solving the second problem. The FIG. 12 flowchart is inserted between the steps S102 and S103 in FIG. 6 or between the steps S202 and S203 in the FIG. 11 flowchart in order to make the focus and the astigmatism of the enlarged specimen image substantially coincident to each other.

Figure 12:
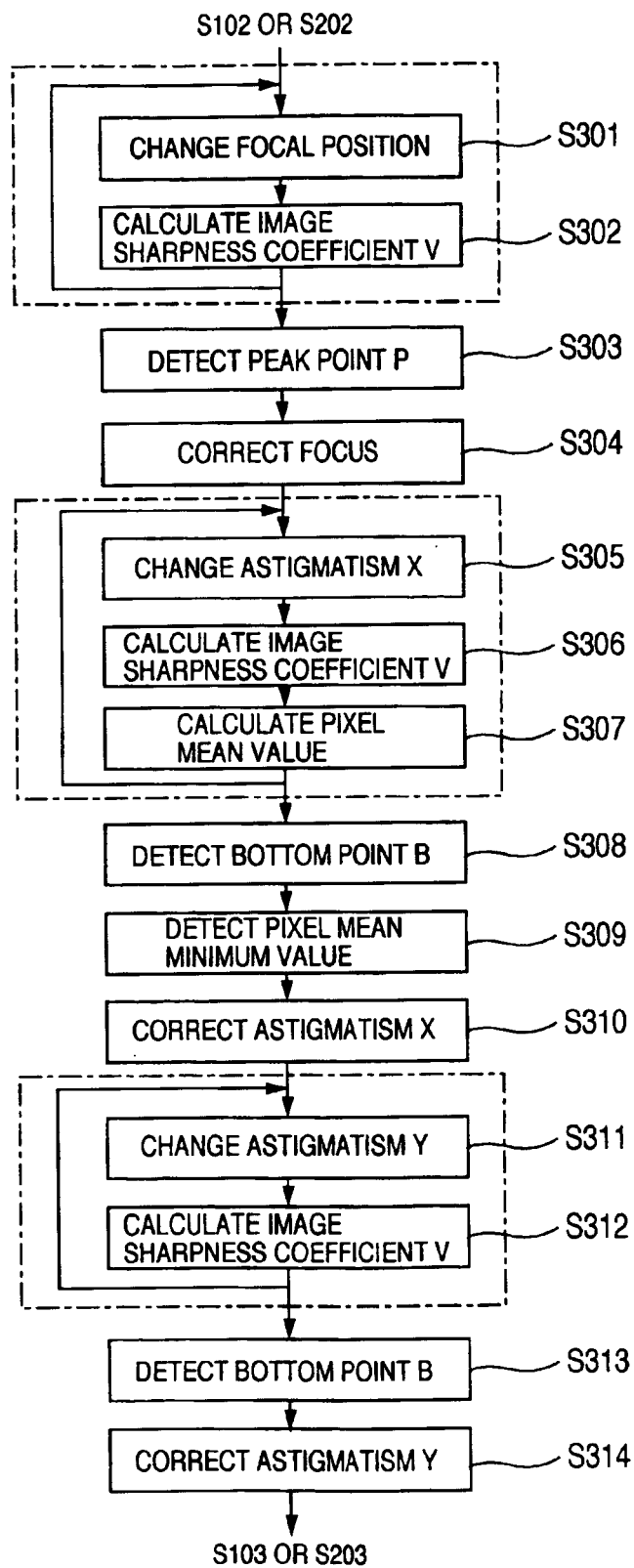
FIG. 12 is a flowchart of focus correction and astigmatism correction to be carried out when a large astigmatic aberration exists and an enlarged specimen image becomes blurred greatly.

After the initial setting in the step S102 in FIG. 6 or the initial setting in the step S202 in FIG. 11 has been completed, the program proceeds to step S301 in FIG. 12. In the step S301, the focal position in the electron microscope is changed and image sharpness coefficients are calculated in step S302. In the present embodiment, an instance is considered in which quite different image pick up conditions are determined immediately after specimen insertion or continuously from the preceding use status. A process in the steps S301 and S302 corresponds to the objective lens coil current change and image sharpness coefficient calculation described in connection with steps S130 to S137 in FIG. 7. Thereafter, in step S303, an image sharpness coefficient peak point is detected. In step S304, an objective lens current for an exact focus is adjusted from the relation between image sharpness coefficient and objective lens coil current. In an alternative, in the step S304, a method may be employed in which an offset amount ΔZ of specimen height is extracted from the relation between image sharpness coefficient peak and objective lens coil current in the step S303 and the height of the specimen stage 10 is calculated by means of the ALU 57 to adjust the focal position. The objective lens current ΔI is related to the specimen height ΔZ in substantially proportional relationship as indicated by equation (19).

$$\Delta Z = \alpha \cdot \Delta I \qquad (19)$$

The steps S301 to S304 are carried out at a low magnification in order for any astigmatism of an enlarged specimen image not to be detected. Though not depicted in the FIG. 12 flowchart, an observation magnification value M1 is set in the step S102 or step S202 and in starting the step S301, the magnification is set to a magnification value M2 lower than M1 and thereafter operation in the steps S301 through S304 is executed. It is to be noted that the electron microscope of this invention has a function to cause the ALU 57 to calculate specimen stage height and specimen height at present and cause the image display unit 59 to display calculation results.

Subsequently, the program proceeds to steps S305 through S307. In this process, the astigmatism correction process shown in FIG. 8 is added with the step S307 of calculating a mean value of pixel values of all pixels.

Figure 18A:
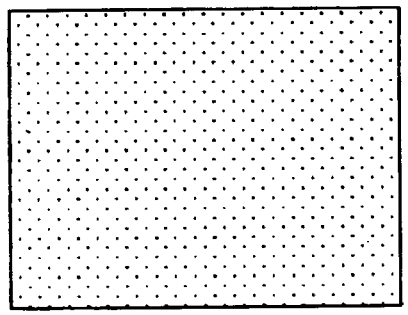
FIG. 18A is a diagram showing an image in the presence of astigmatism to explain hystogram.
Figure 18B:
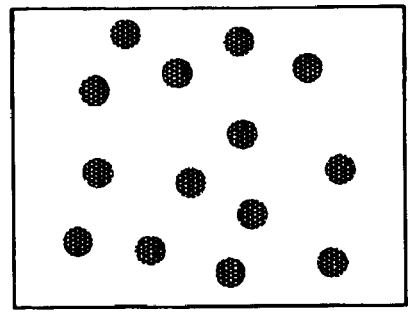
FIG. 18B is a diagram showing an image in the absence of astigmatism to explain hystogram.

The principle of performing the astigmatism correction by using the result of calculation of a mean value of all pixels will be described with reference to FIGS. 18A to 18C and FIG. 19. Illustrated in FIG. 18A is an example of an image when the astigmatism is large. When the astigmatism is large, the image blur is serious, resulting a status that an enlarged structure of a specimen cannot be found and in general, a bright image of low contrast is formed. Illustrated in FIG. 18B is an example of an image in the absence of any astigmatism. With the astigmatism removed, an enlarged structure of a specimen is clearly displayed in the image. In comparison with FIG. 18A, an image of higher contrast can be formed.

Figure 18C:
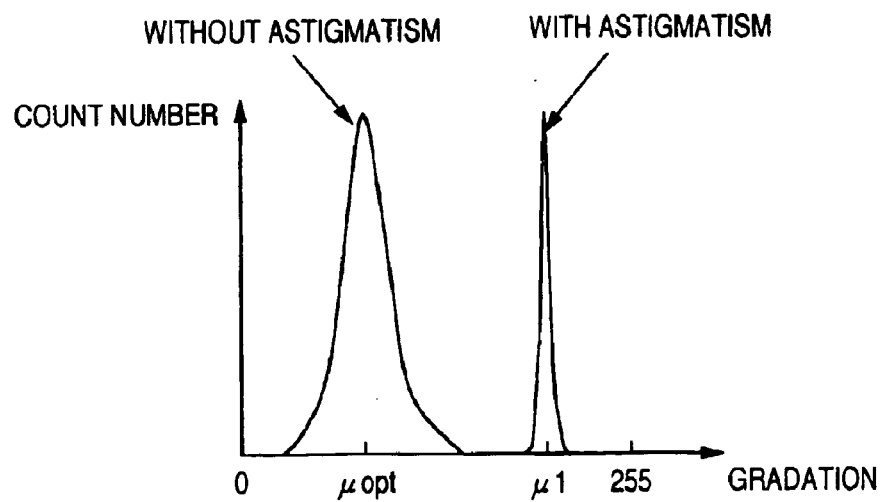
FIG. 18C is a graph useful to explain the relation between the hystogram and the presence or absence of astigmatism.

Shown in FIG. 18C is an example of histogram generally used for image evaluation (an example of 8-bit image). In the histogram, a pixel value (brightness) given to one pixel of a digital image is counted to indicate gradation on abscissa and count number on ordinate. High contrast signifies that brightness values of the image are dispersed widely and bright image signifies that the brightness values are distributed in high gradation. In the event that the image becomes blurred in the presence of an astigmatic aberration as shown in FIG. 8A, histogram of the image occurs at such a position as peak point µ1 where the contrast is low and brightness value is high. On the other hand, when no astigmatism exists as shown in FIG. 18B, the specimen structure is exhibited and histogram occurs at a position $\mu_{opt}$ where the contrast is high and the image is dark.

Figure 19:
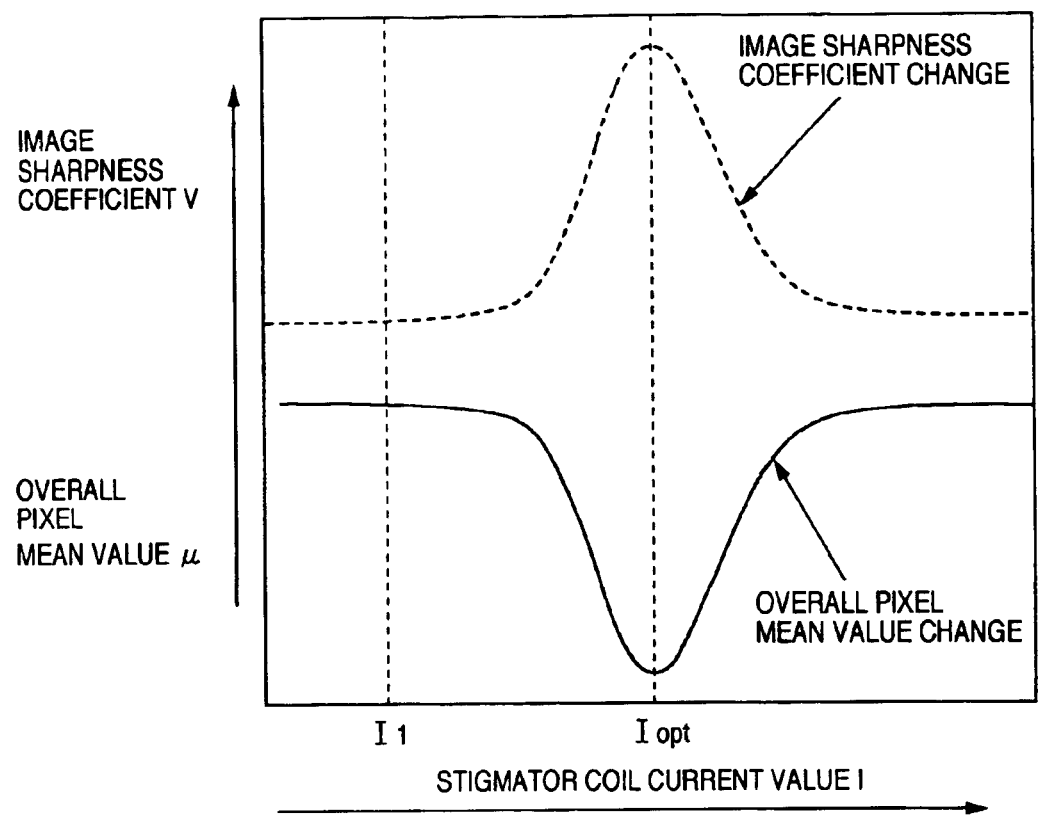
FIG. 19 is a graph showing the relation between stigmator coil current value and image sharpness coefficient or overall pixel mean value.

Referring to FIG. 19, how the image sharpness coefficient and the pixel mean value behave when they are changed by changing the stigmator coil current amount is diagrammatically and graphically illustrated, where abscissa represents stigmator coil current value I and ordinate represents image sharpness coefficient V and pixel mean value of all pixels (overall pixel mean value) µ.

The overall pixel mean value can be expressed by the following equation (20).

$$\mu = \frac{\sum_{i=0}^{255} iC[i]}{\sum_{i=0}^{255} C[i]} \quad (20)$$

In equation (20), i represents the pixel value and C[i] represents the count number of each pixel, indicating that the calculation of overall pixel mean value corresponds to determination of the center of gravity of histogram.

In FIG. 19, $I_1$ corresponds to a stigmator coil current value when the image has an astigmatic aberration as shown in FIG. 18A and $I_{opt}$ corresponds to a stigmator coil current value when the image is devoid of astigmatism as shown in FIG. 18B. In the absence of astigmatism, the contrast is high and the brightness is low and consequently, a value of overall pixel mean value is determined to be the lowest and at that time, the image sharpness coefficient is determined to be the highest. On the other hand, in the presence of astigmatism, the image sharpness coefficient is low and the overall pixel mean value is high. In case astigmatism is displaced largely, the image contrast is reduced as will be seen from the example of the enlarged specimen image of large astigmatism and even if the stigmator coil current is adjusted, an image sharpness coefficient sufficient to form a peak is difficult to attain. As another cause of making the decision difficult with the image sharpness coefficient alone, there occurs such a calculation error that as the image becomes blurred, the contrast is reduced but the S/N (signal to noise ratio) of the image (signal to noise ratio) becomes high and the result of the image sharpness coefficient calculation is indicated to be high. Then, an astigmatism decision based on the overall pixel mean value is added.

In step S308, a bottom point B is detected from the relation between the image sharpness coefficient and the stigmator coil current determined in the step S306. Thereafter, in step S309, the relation between a minimum value of pixel mean value and the stigmator coil current is determined. The bottom point and the stigmator coil current value corresponding to the minimum point are given from the steps S308 and S309, respectively, to correct an astigmatic aberration in X direction. In this phase, if the bottom point B does not coincide with a minimum point based on the profile of the overall pixel mean value, the result of the overall pixel means value is adopted. In the FIG. 12 flowchart, the peak search based on image sharpness coefficient is also performed in the step S306 but if the minimum point can be searched through a method based on overall pixel mean value, the peak search based on the image sharpness coefficient may be omitted. Subsequently, in steps S311 through S314, the stigmator coil in Y direction is corrected approximately. Though not depicted in FIG. 12, when astigmatism is displaced to make the image blur large, there is a possibility that the focus correction is difficult to achieve. Then, in the focus correction process in the steps S301 and S302, the focus correction may be carried out on the basis of the overall pixel mean value. Similarly, in the y-direciton astigmatism correction, too, the image sharpness coefficient V may be calculated in the step S312 and thereafter, like the routine of S307, the pixel mean value may be calculated and an astigmatism correction value may be chosen from results of calculation of the pixel mean value.

Figure 13:
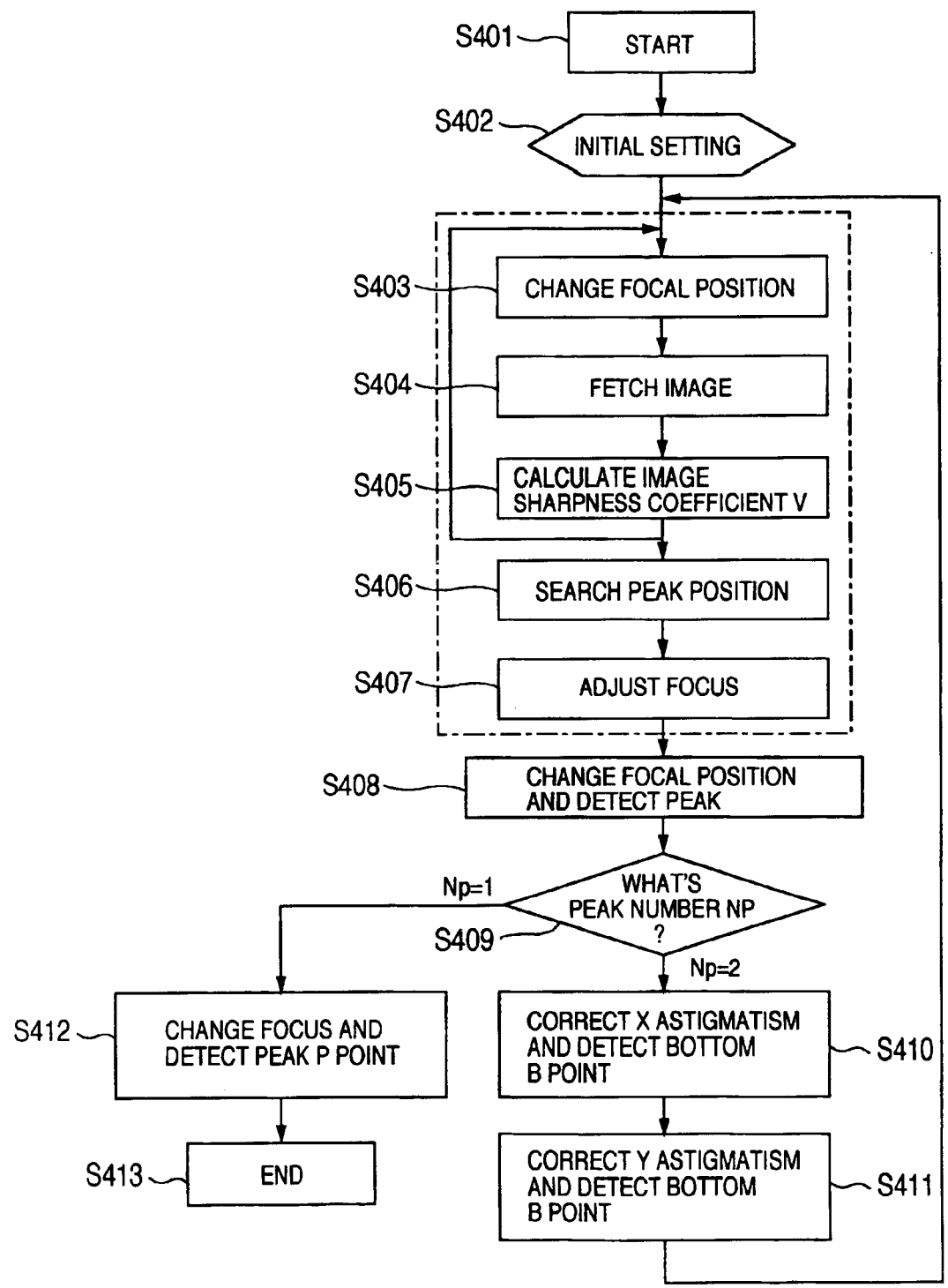
FIG. 13 is a flowchart of focus correction and astigmatism correction when an focus offset is large.

Referring now to a flowchart in FIG. 13, a fourth embdiment of this invention will be described. The present embodiment is directed to show a method for performing focus adjustment and astigmatism correction when the focus is defocused largely under a condition immediately succeeding insertion of a specimen or under a condition that the condition of picking-up an enlarged specimen image is changed greatly. The flowchart in FIG. 13 shows procedures of bringing the focus substantially to an enlarged specimen image and then correcting the astigmatism and focus when a large defocusing exists.

In steps S401 to S402, the initial setting of the electron microscope is carried out. A process in steps S403 through S406 is for evaluating image sharpness coefficients by changing objective lens coil current and it corresponds to the steps S130 to S138 shown in FIG. 7. In the step S406, a peak position is searched and in step S407, an objective lens coil current value corresponding to the peak position is set to perform approximate correction of focus. In the step S407, a method may be employed in which in place of the focus correction using the objective lens coil current, the focus is adjusted by adjusting the height of the specimen stage. A process in steps S408 to S413 corresponds to the process in the steps S103 to S117 in FIG. 6.

Referring now to a flowchart in FIG. 15, a fifth embodiment of this invention will be described. In the present embodiment, correction is made by taking hysteresis of the objective lens coil and hysteresis of an image integration filter during image pick up into consideration, thereby solving the third problem. Here, an example of focus correction will be taken but the same process can also be used in stigmator coil current adjustment.

Figure 14:
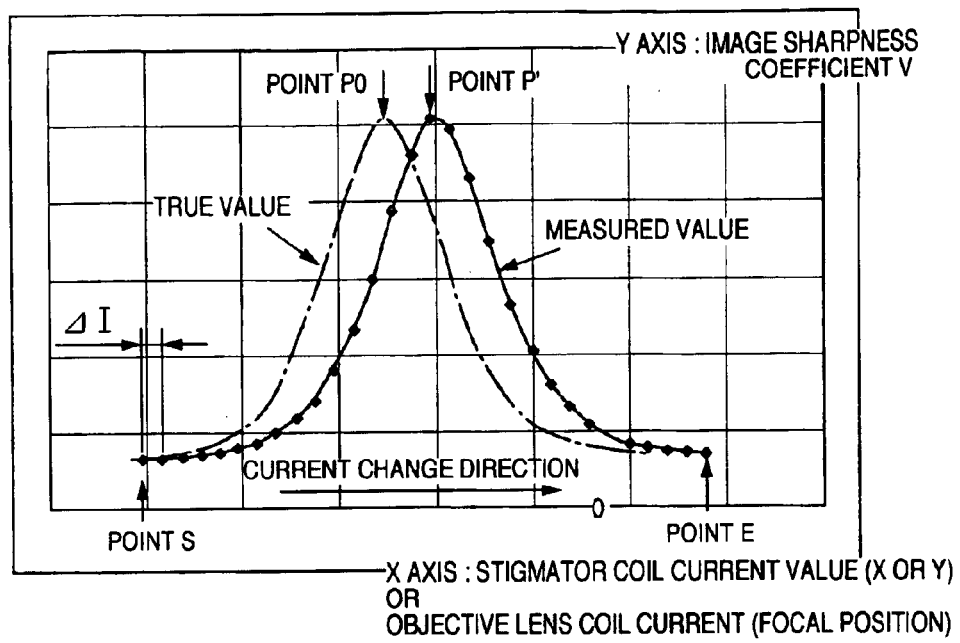
FIG. 14 is a graph of image sharpness coefficients useful to explain the relation between hysteresis and objective lens coil current or stigmator coil current.

The hysteresis will be explained with reference to FIG. 14. A graph in FIG. 14 shows the relation between coil current value and image sharpness coefficient, where abscissa represents objective lens coil current values or stigmator coil current values and ordinate represents image sharpness coefficients.

It is now assumed that the change direction of current is defined as shown by arrow. Further, assumptively, the image sharpness coefficient at each point is calculated by using an enlarged specimen image rendered to have hysteresis of past images in time series by means of an image hysteresis average integration filter and subjected to an averaging process. The use of the hysteresis average integration filter makes it possible to continuously pick up images, so the one enlarged specimen image can be formed in a short time in case of an image of bad S/N and operation time of automatic processing can be shortened to advantage. In this example, the peak of image sharpness coefficient actually calculated is so determined as to be at P' point. But, a true peak point P0 exists earlier than the P' point in the past on time series base. The hysteresis of the lens coil signifies a phenomenon in which when the current is changed to the peak point P' at the exact focal point after current starting from S point has ended at E point, the current cannot return exactly to the P' point because the magnetizing curve of the coil yoke has hysteresis characteristic and becomes non-linear. This problem is solved through a process shown by, for example, the flowchart in FIG. 15.

Figure 15:
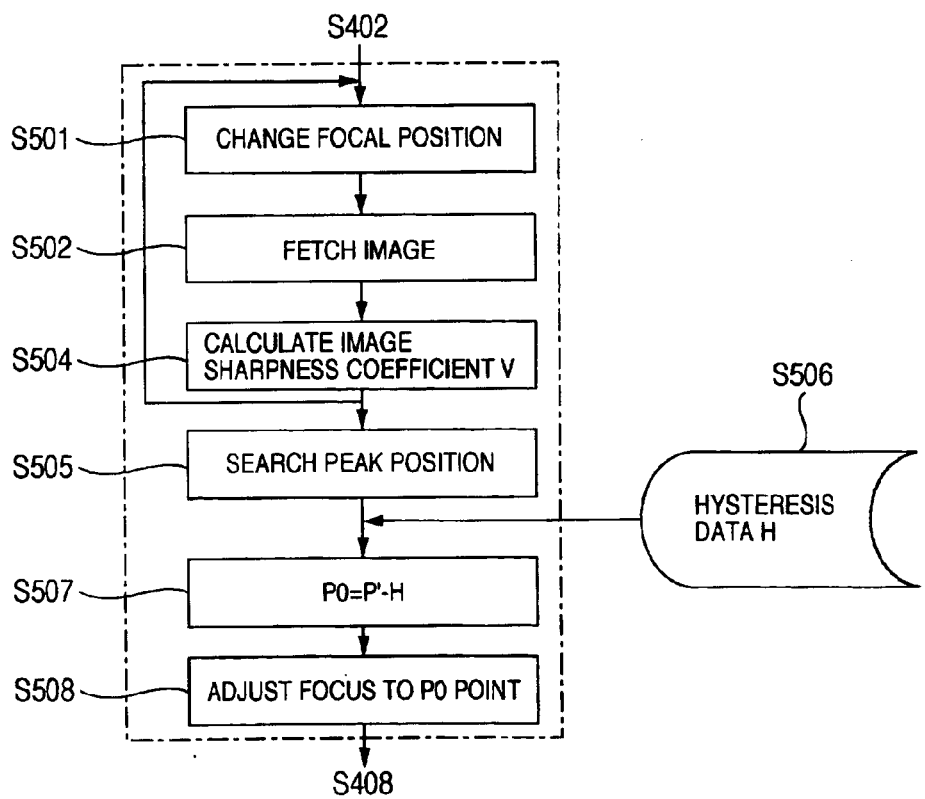
FIG. 15 is a flowchart of a process for performing hysteresis correction.

For example, when the fifth embodiment is applied to the fourth embodiment shown in FIG. 13, the procedure in the steps S403 to S407 in FIG. 13 can be replaced with steps S501 to S508 in FIG. 15. In the step S402 in FIG. 13, the initial setting has been completed and the program proceeds to the step S501. As in the case of the steps S130 to S138 in FIG. 7, operation for preparing the profile of objective lens coil current and image sharpness coefficient is carried out in the steps S501 to S504.

In the step S505, a peak point P' in image sharpness coefficient is detected. Subsequently, in the step S506, hysteresis data H measured and recorded in advance is called out of the ROM. The hysteresis data H is a precedently meansured and determined constant and saved in the ROM in the form of constants different for different apparatus by taking apparatus difference into consideration. In the step S507, a true peak point P0 is determined. The peak point P0 is obtained pursuant to the following equation (21).

$$P_0 = P' - H \quad (21)$$

In the step S508, the objective lens coil current value is set to P0 point, thus completing the focus correction. Subsequently, the program proceeds to the step S408 in FIG. 13. Correction of hysteresis has been described herein by way of example of hysteresis of the objective lens. Similar hysteresis correction is effective for astigmatism correction current setting in the stigmator coil in the steps S410 or S411.

Referring to a flowchart in FIG. 17, a sixth embodiment will be described. In the present embodiment, such an erroneous operation that the contrast of an enlarged specimen image is degraded as the focus defocuses and the peak on the image sharpness coefficient curve is not detected correctly can be prevented, thereby solving the fourth problem. Here, the focus correction is taken as an example but the same process can also be used in the stigmator coil current adjustment.

Figure 16A:
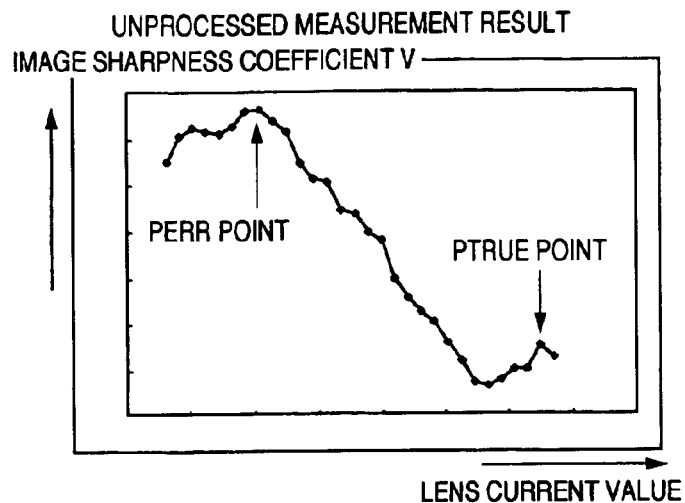
FIG. 16A is a graph for explaining the relation between lens current value and image sharpness coefficient.
Figure 16B:
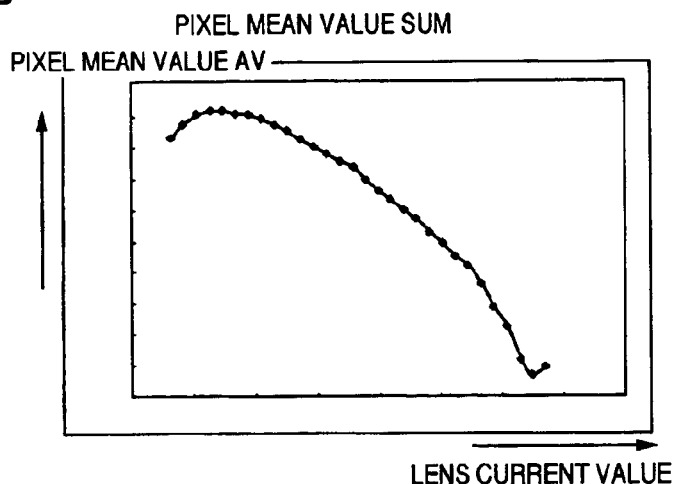
FIG. 16B is a graph for explaining the relation between lens current value and pixel mean value.
Figure 16C:
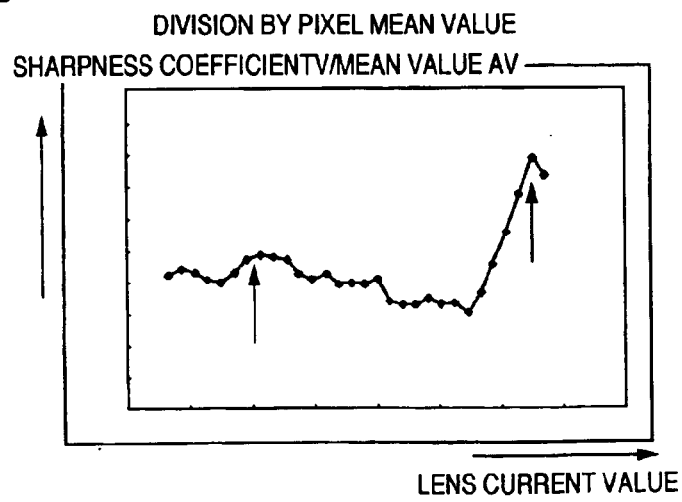
FIG. 16C is a graph showing results of division of image sharpness coefficient by pixel mean value in relation to lens current value.

This problem will be explained with reference to FIGS. 16A to 16C. When performing auto focusing based on image sharpness coefficient, a peak position affected by changes in brightness and contrast of an image is sometimes detected erroneously, resulting in an erroneous operation. Shown in graphs of FIGS. 16A to 16C is the relation between image sharpness coefficient and focal position (objective lens coil current value). Abscissa represents objective lens coil excitation current values.

Depicted in FIG. 16A is an example of unprocessed measurement results, showing an objective lens coil current-image sharpness coefficient curve when a point Perr is determined to be mistaken for a true exact focal position Ptrue. At the Perr point, there is a defocus and an image blur takes place, so that brightness is high over the entire image and the image contrast is low. In respect of this enlarged specimen image, individual mean values of all pixels are calculated and plotted in relation to the objective lens current as shown in FIG. 16B. As the focus defocuses, the brightness of image becomes high and as the image contrast lowers, the pixel mean value becomes high. To avoid such an erroneous decision, image sharpness coefficients corresponding to the respective objective lens coil current values are divided by the overall pixel mean value as shown in FIG. 16C, thereby obtaining the Ptrue point correctly.

A flowchart in FIG. 17 will be described. For example, the initial setting has been completed in the step S402 in FIG. 13 and the program proceeds to step S601 in FIG. 17. In a process of steps S601 to S610, the repetitive process of image sharpness coefficient peak search in the steps S501 to S508 in FIG. 15 is added with step S605 of a process for calculation of pixel mean values of an image. Next, in step S606, the process for dividing the image sharpness coefficient V by the overall pixel mean value μ is carried out to determine a normalized image sharpness coefficient Vn.

$$V_n = \frac{V}{\mu} \quad (22)$$

In step S607, from the profile of objective lens coil current value and normalized image sharpness coefficient as shown in FIG. 16C, a peak position P' of image sharpness coefficient is searched. The hysteresis data H precedently recorded on the ROM is called out in step S608, a peak point P0 considering the hysteresis is determined in step S609 and an objective lens coil current value providing an exact focus is delivered in step S610. After this process, the program returns to the step S408 in FIG. 13.

A seventh embodiment will be described using FIG. 20. In this embodiment, in making auto astigmatism correction, an astigmatic difference is calculated and an astigmatism correction range is automatically detected, thus solving the fifth problem.

Figure 20:
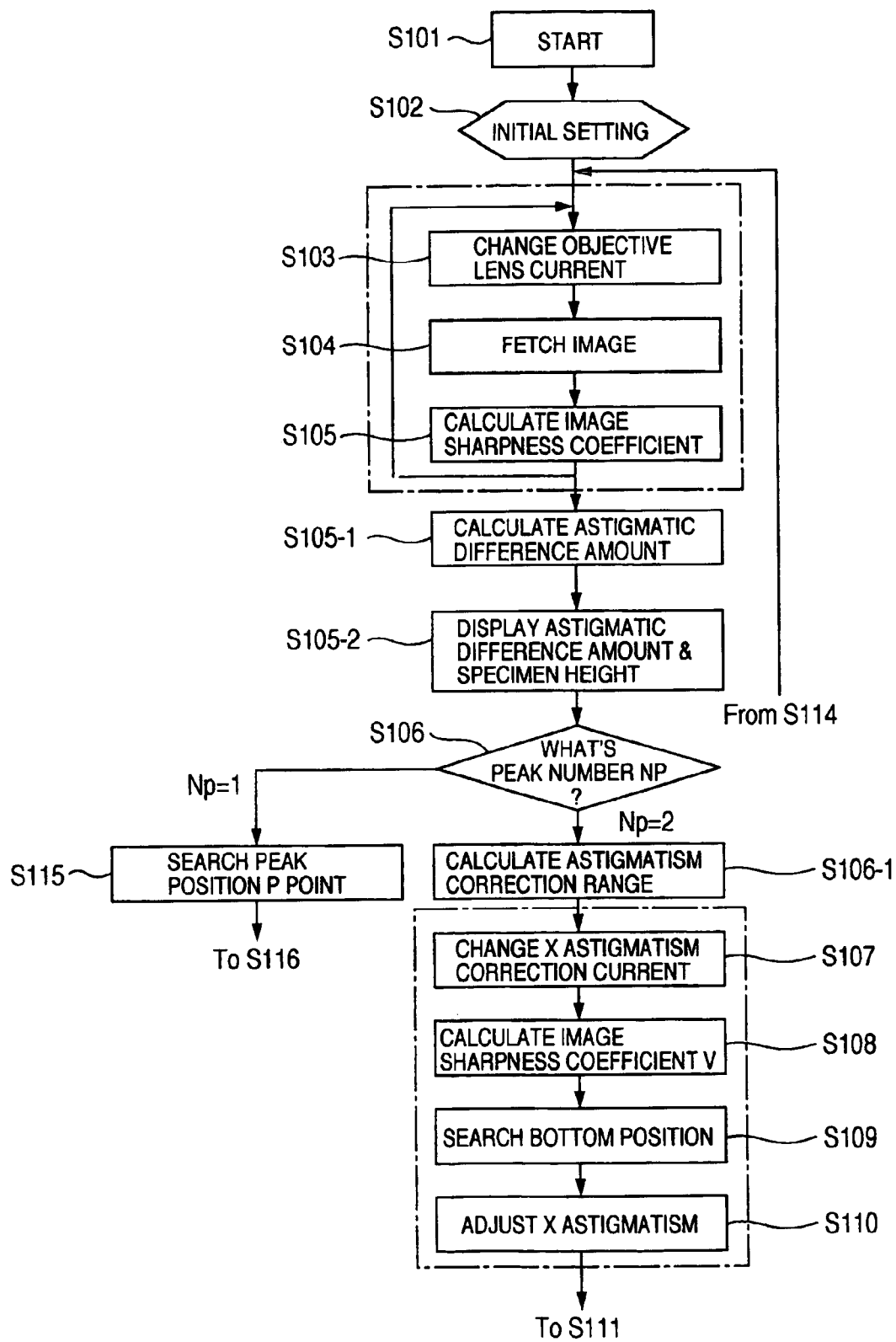
FIG. 20 is a flowchart in which the FIG. 6 astigmatism correction flowchart is added with a routine for determining an astigmatism search range.

In FIG. 20, a flow of detecting an astigmatism correction range is added to the auto astigmatism correction routine shown in FIG. 6. In a routine of steps S103 to S105, respective image sharpness coefficients are calculated using images picked up by changing the objective lens excitation current. In this phase, the objective lens coil excitation current is changed for the purpose of changing the focal position and in alternative, the focus may be changed through a method in which images are picked up and fetched by changing the height of the specimen stage 10 momently. For calculation of the image sharpness coefficients in the stpes S103 to S105, a method may be employed which uses the normalized image sharpness coefficient expressed by equation (22) in embodiment 6. In the presence of an astigmatic aberration, the objective lens excitation current value is related to the image sharpness coefficient as shown in FIG. 4B. Astigmatic difference δfa can be obtained by subtracting an objective lens current value at P2 point from an objective lens current value at P1 point.

$$\delta_{fa} = |(I_{P1} - I_{P2})| \quad (23)$$

In step S105-1, an astigmatic difference amount is calculated on the basis of equation (23). After the astigmatic difference amount has been calculated, the program proceeds to step S106. On the assumption that an astigmatic aberration now exists, Np=2 indicative of the presence of two peak points is concluded and the program proceeds to step S1601-1. In the step S106-1, an astigmatism search range is determined from the astigmatic difference pursuant to equation (23). In the astigmatism correction according to this invention, the range of search of astigmatism must be set in advance and for example, when a large astigmatic aberration in excess of the astigmatism search range exists, searching cannot be done. Then, it is necessary that the magnitude of the astigmatic aberration be calculated from the astigmatic difference and a suitable search range be given.

Figure 21:
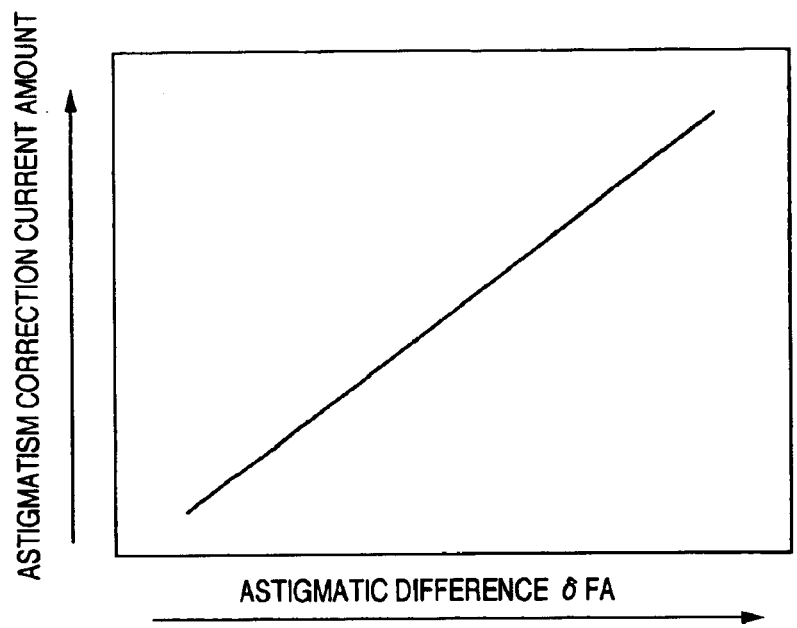
FIG. 21 is a graph showing the relation between astigmatic difference amount and astigmatism search range.

A graph showing the relation between astigmatic difference and astigmatism search range is illustrated in FIG. 21, where abscissa represents astigmatic difference δfa and ordinate represents astigmatism search range. As shown in FIG. 21, within a range in which the objective lens coil excitation current does not changes largely, linearity can be maintained.

For calculation of the astigmatism search range in the step S106-1, the relation between objective lens current value and profile of image sharpness coefficient as shown in FIG. 4B is used. More particularly, in the case of FIG. 20, the repetitive flow of fetching images by changing objective lens current and calculating image sharpness coefficients is carried out in the steps S103 to S105, so that the profile shown in FIG. 4B can be obtained in the presence of astigmatism and an astigmatic difference δfa can be calculated from the profile pursuant to equation (23). The astigmatism search range can be determined from the linear relation between astigmatic difference amount and astigmatism correction current amount. After the astigmatism search range has been calculated in the step S106-1, the program proceeds to a process of changing astigmatism correction current in step S107.

Figure 22:
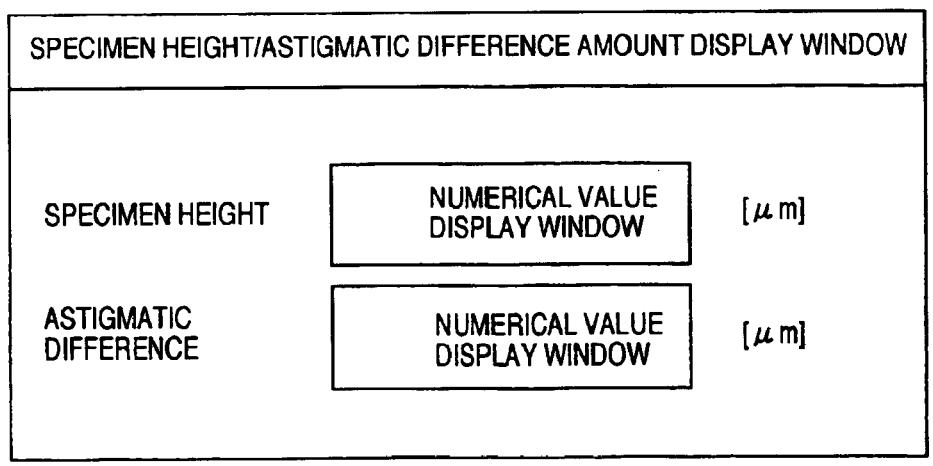
FIG. 22 is a diagram showing an example of a display window for displaying specimen height and astigmatic difference amount.

In the flowchart in FIG. 20, the routine for displaying the astigmatic difference amount and specimen height is annexed to the step S105-2 but the step S105-2 is unnecessary if displaying these values is unneeded. FIG. 22 shows an example of a window to be displayed in the step S105-2.

By using the electron microscope shown in FIG. 1, an eighth embodiment will be described. In the present embodiment, when performing the auto astigmatism correction, the astigmatic difference amount is calculated, displayed quantitatively and compared with a threshold value to decide whether the astigmatism correction has been completed, thus solving the sixth problem.

Figure 23:
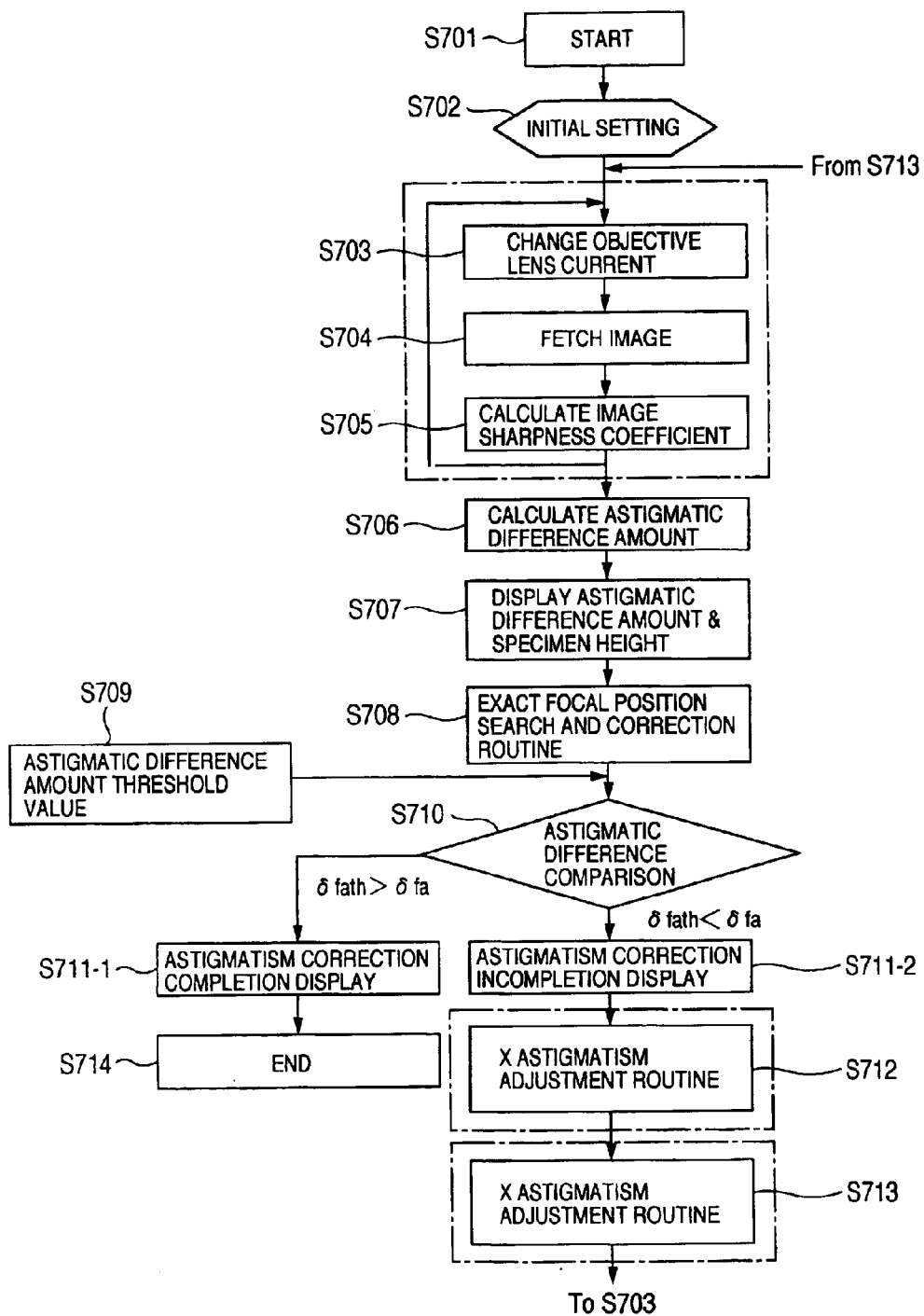
FIG. 23 is a flowchart of calculating an astigmatic difference amount with an electron microscope adapted to perform focusing and astigmatism correction and deciding, from the result of calculation of astigmatic difference amount, whether the operation has been completed.

A flowchart in FIG. 23 shows a flow in which with the electron microscope capable of performing auto focusing and astigmatism correction, an astigmatic difference is calculated from the status of the electron microscope at present, the calculated difference is compared with a predetermined threshold value of astigmatic difference amount to quantitatively decide whether the astigmatism correction has been completed and if completion is concluded, the astigmatism correction routine is ended without being carried out, thereby ensuring that operation time of astigmatism correction operation can be reduced.

In step S701, the use of this electron microscope is started and a desired specimen 11 is mounted to the specimen stage 10 and inserted to the electron microscope. In step S702, initial condition setting is carried out, including setting of magnification, setting of electron beam acceleration voltage and setting of currents to individual coils and individual deflection coil systems. In a routine of steps S703 through S705, images are picked up and fetched by changing the excitation current to the objective lens coil and image sharpness coefficients are calculated in respect of the individual images. In this phase, the excitation current of the objective lens coil is changed for the purpose of changing the focal position and therefore, in an alternative, images may be picked up and fetched by changing the focus through a method in which the height of the specimen stage 10 is changed moment by moment. Further, for calculation of the image sharpness coefficient in the steps S703 to S705, the method using the normalized image sharpness coefficient expressed by equation (22) in embodiment 6 may be adopted.

Figure 24A:
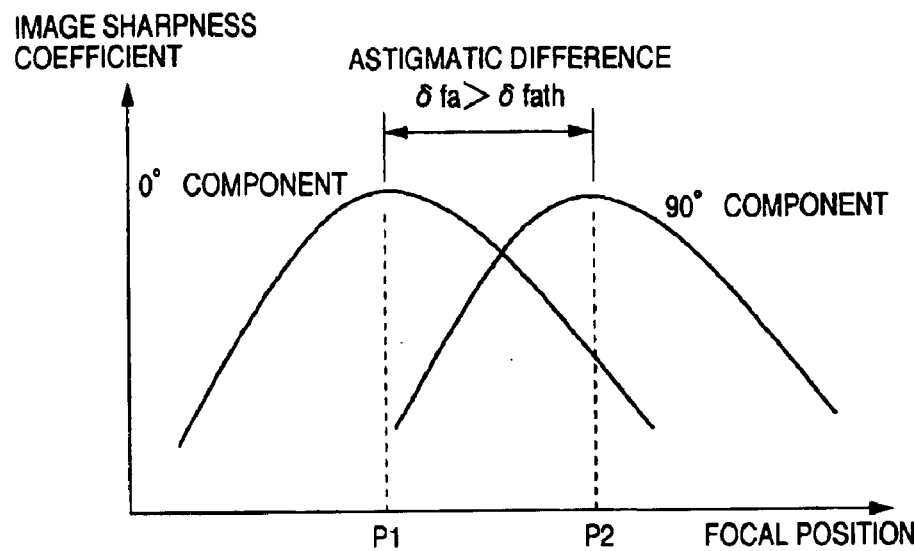
FIG. 24A is a graph showing the relation between image sharpness coefficient and focal position to explain comparison between astigmatic difference threshold value and astigmatic difference amount at present in the presence of a large astigmatism.

In step S706, an astigmatic difference amount is calculated from the result of image calculation in the routine of previous stage. In an optical system having astigmatism, the profile of focal position and image sharpness coefficient as shown in FIG. 4B is plotted. In FIG. 4B, the average of square sum of squared four directional components at 0°, 45°, 90° and 135° is taken to provide the profile but profiles as shown in FIGS. 9A to 9C or FIGS. 10A to 10C may be expressed in which the focal positions and the image sharpness coefficients are indicated independently of each other in respect of the four directional components. In the step S706, the astigmatic distance δfa is determined from the profile as shown in FIG. 4B. In the case of the four-direction divisional profiles, the astigmatic difference is calculated from the difference between focal positions at maximum points in the profiles of 0° and 90° components or 45° and 135° components. The astigmatic difference in this case will be indicated as below by using FIGS. 24A and 24B. An example of profile showing the focal position and image sharpness coefficient is graphically and schematically shown in FIGS. 24A and 24B by limiting the angular components to those at 0° and 90°. Illustrated in FIG. 24A is an instance where the astigmatic difference is large, indicating that the astigmatic difference can be given by equation (24) on the basis of a focal position P1 at which the peak of 0° component takes place and a focal position P2 at which the peak of 90° component takes place.

$$\delta_{fa} = |(P_1 - P_2)| \tag{24}$$

Figure 25:
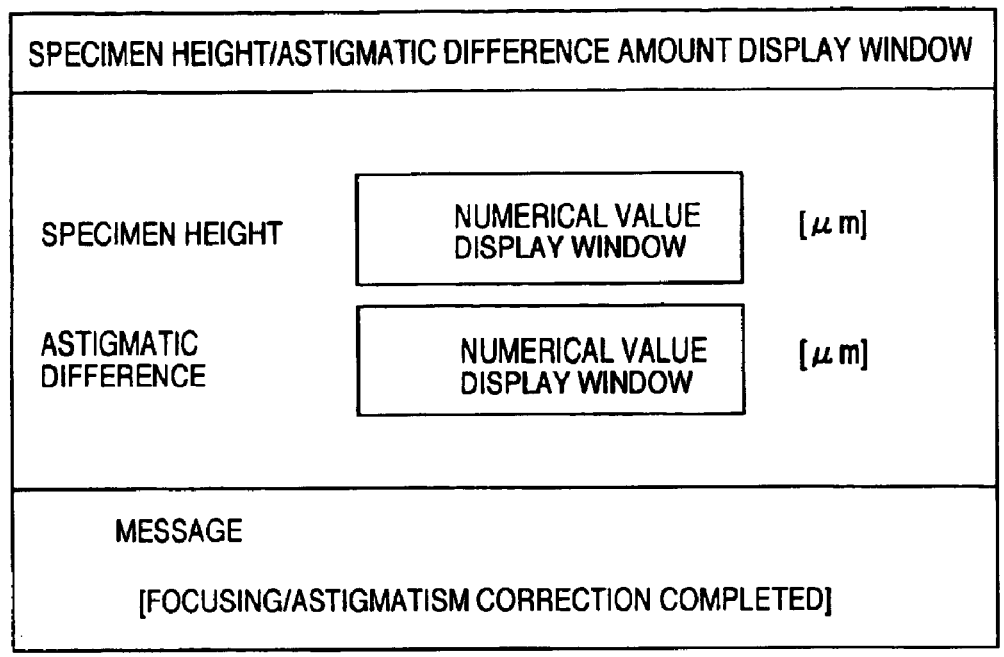
FIG. 25 is a diagram showing an example of a display window for displaying specimen height, astigmatic difference amount and operational state of astigmatism correction.

On the basis of the astigmatic difference obtained pursuant to equation (24), an astigmatic difference amount is displayed in step S707. The astigmatic difference amount is displayed in the display window as shown in FIG. 22 or 25, for instance. In a routine of step S708, an exact focal position is searched and set on the basis of the profile comprised of the image sharpness coefficient and focal position obtained in the steps S703 and S705. For example, if the astigmatic aberration is nullified completely, focal positions indicative of maximum values of profile of two independent angular components shown in FIG. 24A will coincide with each other and searching of exact focal position determines an exact focal position corresponding to the coincident position. In the presence of astigmatism, focal positions indicative of maximum values of the profile of two independent angular components are separated as shown in FIG. 24A and in this case, a center position of the two points indicates an exact focal position as expressed by equation (25).

$$F = \frac{P_1 + P_2}{2} \tag{25}$$

In step S709, a predetermined threshold value data δfath of astigmatic difference is given. The astigmatic difference threshold value data may be either a result obtained by experimentally determining a limit value of the apparatus or a focal depth obtained from an illumination angle to specimen inherent in the electron microscope and a pixel size.

In step S710, the astigmatic difference amount at present obtained in the step S706 is compared with the astigmatic difference threshold value given in the step S709. When the comparison result indicates that the astigmatic difference amount at present is determined to be larger than the astigmatic difference threshold value (δfath<δfa), the program proceeds to step S711-2 to display incompletion of astigmatism correction in the display window shown in FIG. 25. Under this condition, the relation between focal position and image sharpness coefficient profile indicating the astigmatic difference is profiled as shown in FIG. 24A. Thereafter, an astigmatism correction routine in X direction is carried out in step S712 and an astigmatism correction routine in Y direction is carried out in step S713. In the steps S712 and S713, the astigmatism correction flow shown in FIG. 8 is not depicted explicitly. After the step S713 has been completed, the program returns to the step S703 to repeat operation.

Figure 24B:
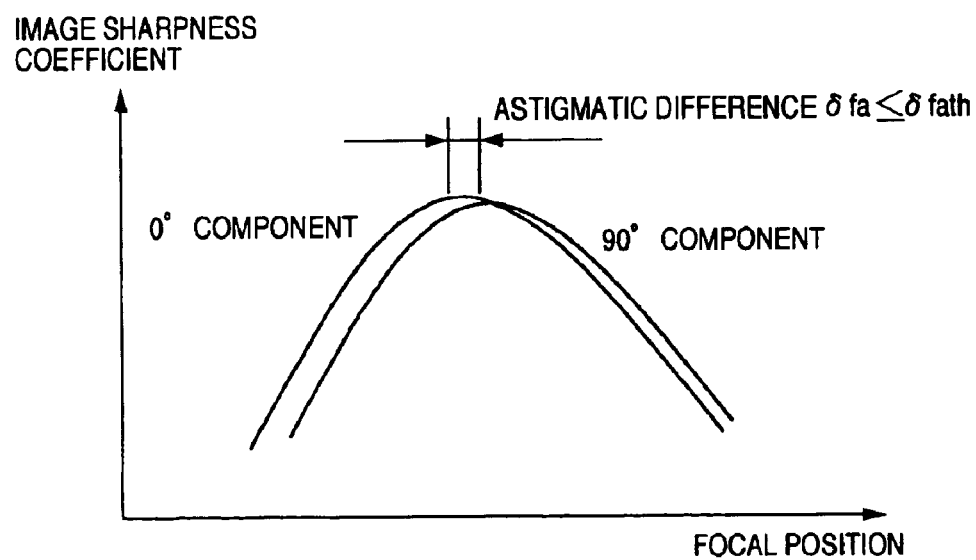
FIG. 24B is a graph showing the relation between image sharpness coefficient and focal position to explain comparison between astigmatic difference threshold value and astigmatic difference amount at present in the presence of a small astigmatism.

When the comparison result in the step S710 indicates that the astigmatic difference amount at present is determined to be smaller than the astigmatic difference threshold value (δfath≧δfa), the program proceeds to step S711-1 to display completion of astigmatism correction in the display window shown in FIG. 25. Under this condition, the relation between focal position and profile of image sharpness coefficient indicating the astigmatic difference is profiled as shown in FIG. 24B, for example. Thereafter, the program proceeds to step S714 to complete the auto focusing and astigmatism correction operation.

In the eighth embodiment, by calculating the astigmatic difference amount during auto astigmatism correction, the astigmatic difference amount can be displayed quantitatively and can be compared with the threshold value to decide whether the astigmatism correction has been completed. Thus, even when the operator of the electron microscope is poor in use experience and cannot understand optimum focusing/astigmatism correction image state, the quantitatively given astigmatism correction image can permit the operator to obtain astigmatism/focus images of substantially constant quality with high reproducibility each time that the present flow is executed. Further, when the astigmatism correction has been completed previously, operation can be completed through the present flow by executing only the focus correction without executing the astigmatism correction routine and consequently, operation time can advantageously be reduced to about ⅓.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A specimen observing method based on an electron microscope, comprising:
a step of picking up enlarged specimen images by changing focal position of an electron beam in relation to a specimen;
a step of image-calculating image sharpness coefficients of the enlarged specimen images; and
a step of deciding the number of peaks on a curve indicative of the relation between focal position of the electron beam and image sharpness coefficient,
wherein when two peaks are determined to exist in said decision, an astigmatism correction process proceeds, said astigmatism correction process including:
a step of picking up enlarged specimen images by changing astigmatism correction current of a stigmator in X direction;
a step of image-calculating image sharpness coefficients of the enlarged specimen images;
a step of determining a minimum position sandwiched by two peaks on a curve indicative of the relation between the astigmatism correction current of said stigmator in X direction and the image sharpness coefficient;
a step of setting the astigmatism correction current of said stigmator in X direction to a current value corresponding to said minimum position;
a step of picking up enlarged specimen images by changing astigmatism correction current of a stigmator in Y direction;
a step of image-calculating image sharpness coefficients of the enlarged specimen images;
a step of determining a minimum position sandwiched by two peaks on a curve indicative of the relation between astigmatism correction current of said stigmator in Y direction and image sharpness coefficient; and
a step of setting the astigmatism correction current of said stigmator in Y direction to a current value corresponding to said minimum position.

2. A specimen observing method based on an electron microscope according to claim 1, wherein when two peaks are determined to exist in said decision, said minimum position sandwiched by the two peaks is determined before said astigmatism correction process proceeds and the focal position of the electron beam is set to a position corresponding to said minimum position.

3. A specimen observing method based on an electron microscope, comprising:
a step of picking up enlarged specimen images by changing focal position of an electron beam in relation to a specimen;
a step of image-calculating an angular direction component of image sharpness coefficient of the enlarged specimen image;
a step of deciding an astigmatism correction direction from a result of the calculation of the angular direction component of image sharpness coefficient of said enlarged specimen image;
a step of picking up enlarged specimen images by changing the astigmatism correction current of stigmator in said determined direction;
a step of calculating image sharpness coefficients of said enlarged specimen images;
a step of determining a minimum position sandwiched by two peaks on a curve indicative of the relation between astigmatism correction current of said stigmator and image sharpness coefficient; and
a step of setting the astigmatism correction current of said stigmator to a current value corresponding to said minimum position.

4. A specimen observing method based on an electron microscope according to claim 1, wherein a focus correction process proceeds after the astigmatism correction has been completed, said focus correction process including:
a step of picking up enlarged specimen images by changing focal position of an electron beam in relation to a specimen;
a step of calculating image sharpness coefficients of said enlarged specimen images;

a step of determining a peak position on a curve indicative of the relation between focal position of the electron beam and image sharpness coefficient; and a step of setting the focal position of the electron beam to a position corresponding to said peak position.

5. A specimen observing method based on an electron microscope according to claim 1, wherein the image sharpness coefficient is image-calculated in respect of an edge enhanced image of the enlarged specimen image.

6. A specimen observing method based on an electron microscope for performing a process of making the focus of the electron beam coincident with a specimen after a process of correcting astigmatism of the electron beam, wherein a process of making focal position of the electron beam substantially coincident with the specimen before the process of correcting astigmatism of the electron beam, said process of making focal position of the electron beam substantially coincident with the specimen including:

a step of picking up enlarged specimen images by changing the focal position of the electron beam in relation to the specimen;

a step of calculating pixel mean values of said enlarged specimen images;

a step of determining a minimum position on a curve indicative of the relation between the focal position of said electron beam and the pixel mean value; and a step of setting the focal position of said electron beam to a position corresponding to said minimum position, and said process of correcting astigmatism of the electron beam including the individual steps as recited in any one of claims 1 to 3.

7. A specimen observing method based on an electron microscope for performing a process of focusing an electron beam on a specimen after a process of correcting astigmatism of the electron beam, wherein a process of making focal position of the electron beam substantially coincident with the specimen is carried out before the process of correcting astigmatism of the electron beam, said process of making focal position of the electron beam substantially coincident with the specimen including:

a step of picking up enlarged specimen images by changing focal position of the electron beam in relation to the specimen;

a step of calculating image sharpness coefficients of said enlarged specimen images;

a step of calculating pixel mean values of said enlarged specimen images;

a step of determining a ratio between the image sharpness coefficient and the pixel mean value at each focal position;

a step of determining a maximum position on a curve indicative of the relation between the focal position of the electron beam and the ratio; and a step of setting the focal position of the electron beam to a position corresponding to said maximum position, and said process of correcting astigmatism of the electron beam including the individual steps as recited in any one of claims 1 to 3.

8. A specimen observing method based on an electron microscope according to claim 6, wherein said process of making focal position of the electron beam substantially coincident with said specimen is performed at a lower magnification than a specimen observation magnification.

9. A specimen observing method based on an electron microscope according to claim 1, wherein when setting the astigmatism correction current to a current value corresponding to said minimum position, hysteresis of astigmatism correction current of said stigmator and astigmatism correction amount is taken into account.

10. A specimen observing method based on an electron microscope according to claim 1, wherein the focal position of the electron beam in relation to said specimen is changed by changing excitation current of the objective lens and when setting the focal position of said electron beam to a position corresponding to said minimum position, hysteresis of the excitation current of objective lens and the focal position is taken into consideration.

11. A specimen observing method based on an electron microscope according to claim 1 further comprising a step of, when the number of peaks is determined to be two in said decision, determining an astigmatic difference amount from said two peaks.

12. A specimen observing microscope based on an electron microscope according to claim 11, wherein a range within which said astigmatism correction current is changed is determined on the basis of said astigmatic difference amount.

13. A specimen observing method based on an electron microscope according to claim 11, wherein when the astigmatic difference amount is larger than a predetermined threshold value, said astigmatism correction process proceeds.

14. A specimen observing method based on an electron microscope according to claim 13, wherein measurement of said astigmatic difference amount and said astigmatism correction process are executed repetitively until said astigmatic difference amount becomes smaller than said threshold value.

15. An electron beam apparatus for observing a specimen, the apparatus comprising:

an electron microscope for irradiating the specimen with an electron beam and generating enlarged images of the specimen from the electron beam irradiation of the specimen, the electron microscope including a stigmator; and a controller for controlling operation of the electron microscope, configured to cause the electron microscope to implement steps comprising:

picking up enlarged specimen images by changing focal position of the electron beam in relation to a specimen;

image-calculating image sharpness coefficients of the enlarged specimen images; and deciding the number of peaks on a curve indicative of the relation between focal position of the electron beam and image sharpness coefficient, wherein when two peaks are determined to exist in said decision, an astigmatism correction process proceeds, said astigmatism correction process including:

picking up enlarged specimen images by changing astigmatism correction current of the stigmator in X direction;

image-calculating image sharpness coefficients of the enlarged specimen images;

determining a minimum position sandwiched by two peaks on a curve indicative of the relation between the astigmatism correction current of the stiginator in the X direction and the image sharpness coefficient;

setting the astigmatism correction current of the stigmator in the X direction to a current value corresponding to said minimum position;

picking up enlarged specimen images by changing astigmatism correction current of the stigmator in Y direction;

image-calculating image sharpness coefficients of the enlarged specimen images;

determining a minimum position sandwiched by two peaks on a curve indicative of the relation between astigmatism correction current of the stigmator in the Y direction and image sharpness coefficient; and setting the astigmatism correction current of the stigmator in the Y direction to a current value corresponding to said minimum position.

16. An electron beam apparatus for observing a specimen, the apparatus comprising:

an electron microscope for irradiating the specimen with an electron beam and generating enlarged images of the specimen from the electron beam irradiation of the specimen, the electron microscope including a stigmator; and a controller for controlling operation of the electron microscope, configured to cause the electron microscope to implement steps comprising:

picking up enlarged specimen images by changing focal position of the electron beam in relation to a specimen;

image-calculating an angular direction component of image sharpness coefficient of the enlarged specimen images;

deciding an astigmatism correction direction from a result of the calculation of the angular direction component of image sharpness coefficient of said enlarged specimen images;

picking up enlarged specimen images by changing the astigmatism correction current of the stigmator in said determined direction;

calculating image sharpness coefficients of said enlarged specimen images;

determining a minimum position sandwiched by two peaks on a curve indicative of the relation between astigmatism correction current of the stigmator and image sharpness coefficient; and setting the astigmatism correction current of the stigmator to a current value corresponding to said minimum position.

* * * * *